United States Patent
Hassidov et al.

(10) Patent No.: US 10,322,226 B2
(45) Date of Patent: Jun. 18, 2019

(54) CLEANING METHOD FOR PREPLESS COLONOSCOPY

(71) Applicant: Motus GI Medical Technologies Ltd., Tirat HaCarmel (IL)

(72) Inventors: Noam Hassidov, Moshav Bustan HaGalil (IL); Eyal Kochavi, Haifa (IL); Tzach Arnon, Yodfat (IL); Kobi Luleko, Eshchar (IL)

(73) Assignee: Motus GI Medical Technologies Ltd., Tirat HaCarmel (IL)

( * ) Notice: Subject to any disclaimer, the term of this patent is extended or adjusted under 35 U.S.C. 154(b) by 0 days.

(21) Appl. No.: 15/301,968

(22) PCT Filed: Apr. 8, 2015

(86) PCT No.: PCT/IL2015/050379
§ 371 (c)(1),
(2) Date: Oct. 5, 2016

(87) PCT Pub. No.: WO2015/155776
PCT Pub. Date: Oct. 15, 2015

(65) Prior Publication Data
US 2017/0173256 A1 Jun. 22, 2017

Related U.S. Application Data

(60) Provisional application No. 61/977,173, filed on Apr. 9, 2014.

(51) Int. Cl.
*A61B 1/31* (2006.01)
*A61M 3/02* (2006.01)
*A61M 39/24* (2006.01)

(52) U.S. Cl.
CPC .............. *A61M 3/0283* (2013.01); *A61B 1/31* (2013.01); *A61M 3/02* (2013.01); *A61M 39/24* (2013.01);
(Continued)

(58) Field of Classification Search
CPC ........ A61M 3/0283; A61M 39/24; A61B 1/31
(Continued)

(56) References Cited

U.S. PATENT DOCUMENTS 5,096,385 A 3/1992 Georgi et al.
5,201,908 A 4/1993 Jones
(Continued)

FOREIGN PATENT DOCUMENTS

CN 101301191 11/2008
CN 102046064 5/2011
(Continued)

OTHER PUBLICATIONS

Translation of Notification of Office Action dated Nov. 16, 2017 From the State Intellectual Property Office of the People's Republic of China Re. Application No. 201580037467.6. (2 Pages).
(Continued)

*Primary Examiner* — Phillip A Gray

(57) ABSTRACT

Methods for clearing of fecal matter the wall of a colon or other body lumen for diagnostic inspection, the methods being adapted to clearing of fecal matter comprised of particles of various sizes and compositions. Methods are further adapted for application in patients who have undergone a restricted scope of preparation to reduce and/or remediate the particle structure of colon contents, or no preparation at all, before diagnostic inspection.

8 Claims, 6 Drawing Sheets

(52) U.S. Cl.
CPC ................. *A61M 2202/068* (2013.01); *A61M 2205/3306* (2013.01); *A61M 2205/3327* (2013.01)

(58) Field of Classification Search
USPC ........................................................ 604/28
See application file for complete search history.

(56) References Cited

U.S. PATENT DOCUMENTS

| | | | |
|---|---|---|---|
| 5,279,542 A | 1/1994 | Wilk | |
| 5,554,098 A | 9/1996 | Yabe et al. | |
| 5,630,795 A | 5/1997 | Kuramoto et al. | |
| 5,674,182 A | 10/1997 | Suzuki et al. | |
| 5,679,110 A | 10/1997 | Hamazaki | |
| 5,725,476 A | 3/1998 | Yasui et al. | |
| 5,725,477 A | 3/1998 | Yasui et al. | |
| 5,788,650 A | 8/1998 | Dotolo | |
| 6,309,346 B1 | 10/2001 | Farhadi | |
| 6,409,657 B1 | 6/2002 | Kawano | |
| 6,641,553 B1 | 11/2003 | Chee et al. | |
| D536,449 S | 2/2007 | Nakajima et al. | |
| 2005/0033264 A1 | 2/2005 | Redinger | |
| 2005/0154262 A1 | 7/2005 | Banik et al. | |
| 2005/0256464 A1 | 11/2005 | Pallas | |
| 2006/0025729 A1 | 2/2006 | Leiboff et al. | |
| 2006/0069304 A1 | 3/2006 | Takemoto et al. | |
| 2006/0079861 A1 | 4/2006 | Matasov | |
| 2006/0235458 A1 | 10/2006 | Belson | |
| 2007/0015965 A1 | 1/2007 | Cox et al. | |
| 2007/0234716 A1 | 10/2007 | Hirooka | |
| 2008/0188715 A1 | 8/2008 | Fujimoto | |
| 2009/0143722 A1 | 6/2009 | Kim | |
| 2009/0198212 A1 | 8/2009 | Timberlake et al. | |
| 2009/0292172 A1 | 11/2009 | Roskopf et al. | |
| 2010/0025644 A1 | 2/2010 | Jockisch | |
| 2010/0063358 A1 | 3/2010 | Kessler | |
| 2010/0185150 A1 | 7/2010 | Zacharias | |
| 2010/0256447 A1 | 10/2010 | Dubi et al. | |
| 2010/0298773 A1* | 11/2010 | Nitsan ................. | A61M 3/0283 604/150 |
| 2011/0034865 A1* | 2/2011 | Wallace .............. | A61M 3/0283 604/28 |
| 2011/0092892 A1* | 4/2011 | Nitsan ................. | A61B 1/00068 604/28 |
| 2011/0105845 A1 | 5/2011 | Gordon et al. | |
| 2012/0101336 A1 | 4/2012 | Hirsch et al. | |
| 2012/0289910 A1 | 11/2012 | Shtul et al. | |
| 2013/0085442 A1* | 4/2013 | Shtul .................... | A61B 1/015 604/28 |
| 2013/0296771 A1 | 11/2013 | Shtul et al. | |
| 2015/0257633 A1 | 9/2015 | Hassidov et al. | |
| 2016/0206805 A1 | 7/2016 | Hassidov et al. | |
| 2016/0324412 A1 | 11/2016 | Hassidov et al. | |
| 2018/0020905 A1 | 1/2018 | Chouinard et al. | |
| 2018/0235448 A1 | 8/2018 | Hassidov et al. | |

FOREIGN PATENT DOCUMENTS

| | | |
|---|---|---|
| CN | 102076271 | 5/2011 |
| DE | 3624428 | 1/1988 |
| EP | 1284120 | 2/2003 |
| EP | 1508294 | 2/2005 |
| EP | 2417896 | 2/2012 |
| JP | 50-81088 | 11/1973 |
| JP | 59-183202 | 12/1984 |
| JP | 05-161711 | 6/1993 |
| JP | 06-066605 | 9/1994 |
| JP | 07-155283 | 6/1995 |
| JP | 07-178040 | 7/1995 |
| JP | 11-216104 | 8/1999 |
| JP | 2000-014767 | 1/2000 |
| JP | 2001-061760 | 3/2001 |
| JP | 2003-265595 | 9/2003 |
| JP | 2004-008822 | 1/2004 |
| JP | 2004-357846 | 12/2004 |
| JP | 2005-095582 | 4/2005 |
| JP | 2005-137423 | 6/2005 |
| JP | 2006-325816 | 12/2006 |
| JP | 2007-278191 | 10/2007 |
| JP | 2007-536073 | 12/2007 |
| JP | 2008-532727 | 8/2008 |
| JP | 2008-206559 | 9/2008 |
| JP | 2011-083329 | 4/2011 |
| JP | 2011-518584 | 6/2011 |
| JP | 2011-520567 | 7/2011 |
| JP | 2013-516300 | 5/2013 |
| JP | 2013-532023 | 8/2013 |
| WO | WO 92/17219 | 10/1992 |
| WO | WO 99/60934 | 12/1999 |
| WO | WO 00/54653 | 9/2000 |
| WO | WO 01/12102 | 2/2001 |
| WO | WO 2005/110580 | 11/2005 |
| WO | WO 2005/117685 | 12/2005 |
| WO | WO 2006/039511 | 4/2006 |
| WO | WO 2006/101908 | 9/2006 |
| WO | WO 2008/093288 | 8/2008 |
| WO | WO 2008/155776 | 12/2008 |
| WO | WO 2009/040744 | 4/2009 |
| WO | WO 2009/095915 | 8/2009 |
| WO | WO 2009/125387 | 10/2009 |
| WO | WO 2009/143201 | 11/2009 |
| WO | WO 2010/138521 | 12/2010 |
| WO | WO 2011/083450 | 7/2011 |
| WO | WO 2011/083451 | 7/2011 |
| WO | WO 2011/158232 | 12/2011 |
| WO | WO 2015/029039 | 3/2015 |
| WO | WO 2015/075721 | 5/2015 |
| WO | WO 2015/155776 | 10/2015 |
| WO | WO 2015/193896 | 12/2015 |
| WO | WO 2016/189533 | 12/2016 |

OTHER PUBLICATIONS

International Preliminary Report on Patentability dated Dec. 7, 2017 From the International Bureau of WIPO Re. Application No. PCT/IL2016/050544. (8 Pages).
Supplementary European Search Report and the European Search Opinion dated Dec. 1, 2017 From the European Patent Office Re. Application No. 15776016.6. (10 Pages).
Communication Pursuant to Article 94(3) EPC dated Jan. 3, 2017 From the European Patent Office Re. Application No. 15735746.8. (4 Pages).
Communication Relating to the Results of the Partial International Search dated Feb. 24, 2015 From the International Searching Authority Re. Application No. PCT/IL2014/051014.
International Preliminary Report on Patentability dated Jun. 2, 2016 From the International Bureau of WIPO Re. Application No. PCT/IL2014/051014.
International Preliminary Report on Patentability dated Mar. 10, 2016 From the International Bureau of WIPO Re. Application No. PCT/IL2014/050778.
International Preliminary Report on Patentability dated Oct. 20, 2016 From the International Bureau of WIPO Re. Application No. PCT/IL2015/050379. (9 Pages).
International Preliminary Report on Patentability dated Dec. 29, 2016 From the International Bureau of WIPO Re. Application No. PCT/IL2015/050615. (8 Pages).
International Search Report and the Written Opinion dated May 6, 2015 From the International Searching Authority Re. Application No. PCT/IL2014/051014.
International Search Report and the Written Opinion dated Dec. 8, 2014 From the International Searching Authority Re. Application No. PCT/IL2014/050778.
International Search Report and the Written Opinion dated Sep. 11, 2016 From the International Searching Authority Re. Application No. PCT/IL2016/050544.
International Search Report and the Written Opinion dated Oct. 13, 2015 From the International Searching Authority Re. Application No. PCT/IL2015/050615.

(56) References Cited

OTHER PUBLICATIONS

International Search Report and the Written Opinion dated Feb. 16, 2016 From the International Searching Authority Re. Application No. PCT/IL2015/050379.
International Search Report and the Written Opinion dated Oct. 16, 2015 From the International Searching Authority Re. Application No. PCT/IL2015/050379.
Invitation to Pay Additional Fees dated Aug. 12, 2015 From the International Searching Authority Re. Application No. PCT/IL2015/050379.
Notice of Reason for Rejection dated Jan. 31, 2017 From the Japan Patent Office Re. Application No. 2016-553662. (3 Pages).
Restriction Official Action dated Nov. 16, 2016 From the US Patent and Trademark Office Re. U.S. Appl. No. 14/722,400. (11 pages).
Ambrose et al. "Physiological Consequences of Orthograde Lavage Bowel Preparation for Elective Colorectal Surgery: A Review", Journal of the Royal Society of Medicine,76(9): 767-771, Sep. 1983. p. 768, 2nd Paragraph.
Translation of Notice of Grounds of Rejection dated Jan. 31, 2017 From the Japan Patent Office Re. Application No. 2016-553662. (4 Pages).
Restriction Official Action dated Feb. 28, 2017 From the US Patent and Trademark Office Re. U.S. Appl. No. 14/722,400. (11 pages.
Restriction Official Action dated Mar. 29, 2017 From the US Patent and Trademark Office Re. U.S. Appl. No. 15/108,601. (10 Pages).
Official Action dated May 31, 2017 From the US Patent and Trademark Office Re. U.S. Appl. No. 15/108,601. (46 Pages).
Official Action dated Jun. 6, 2017 from the US Patent and Trademark Office Re. U.S. Appl. No. 14/722,400. (51 pages).
Applicant-Initiated Interview Summary dated Sep. 14, 2017 From the US Patent and Trademark Office Re. U.S. Appl. No. 15/108,601. (3 pages).
Official Action dated Oct. 19, 2017 From the US Patent and Trademark Office Re. U.S. Appl. No. 15/108,601. (38 pages).
Official Action dated Nov. 8, 2017 From the US Patent and Trademark Office Re. U.S. Appl. No. 14/722,400. (23 pages).
Notification of Office Action and Search Report dated Nov. 16, 2017 From the State Intellectual Property Office of the People's Republic of China Re. Application No. 201580037467.6. (9 Pages).
Restriction Official Action dated Jan. 16, 2018 From the US Patent and Trademark Office Re. U.S. Appl. No. 14/915,266. (8 pages).
Applicant-Initiated Interview Summary dated Aug. 4, 2017 From the US Patent and Trademark Office Re. U.S. Appl. No. 14/722,400. (3 Pages).
Translation of Notice of Grounds of Rejection dated Jun. 27, 2017 From the Japan Patent Office Re. Application No. 2016-553662. (3 Pages).
Notice of Reason for Rejection dated Jun. 27, 2017 From the Japan Patent Office Re. Application No. 2016-553662. (3 Pages).
Notice of Reasons for Rejection dated Jul. 10, 2018 From the Japan Patent Office Re. Application No. 2016-537600 and Its Summary in English. (9 Pages).
Notice of Allowance dated Dec. 5, 2018 From the US Patent and Trademark Office Re. U.S. Appl. No. 14/915,266. (18 pages).
Notice of Grounds of Rejection dated Nov. 6, 2018 From the Japan Patent Office Re. Application No. 2017-227752. (2 Pages).
Translation Dated Nov. 14, 2018 of Notice of Grounds of Rejection dated Nov. 6, 2018 From the Japan Patent Office Re. Application No. 2017-227752. (2 Pages).
Translation Dated Jul. 24, 2018 of Notice of Reasons for Rejection dated Jul. 10, 2018 From the Japan Patent Office Re. Application No. 2016-537600 and Its Summary in English. (9 Pages).
Notice of Grounds of Rejection dated Sep. 5, 2018 From the Japan Patent Office Re. Application No. 2016-528831. (6 Pages).
Restriction Official Action dated Oct. 4, 2018 From the US Patent and Trademark Office Re. U.S. Appl. No. 15/959,397. (10 pages).
Translation Dated Sep. 20, 2018 of Notice of Grounds of Rejection dated Sep. 5, 2018 From the Japan Patent Office Re. Application No. 2016-528831. (7 Pages).
Official Action dated Apr. 5, 2018 From the US Patent and Trademark Office Re. U.S. Appl. No. 14/915,266. (62 pages).
European Search Report and the European Search Opinion dated Mar. 23, 2018 From the European Patent Office Re. Application No. 17196947.0. (7 Pages).
Notice of Reasons for Rejection dated Feb. 6, 2019 From the Japan Patent Office Re. Application No. 2016-559518 and Its Translation Into English. (12 Pages).
Official Action dated Mar. 15, 2019 From the US Patent and Trademark Office Re. U.S. Appl. No. 14/722,400. (41 pages).

\* cited by examiner

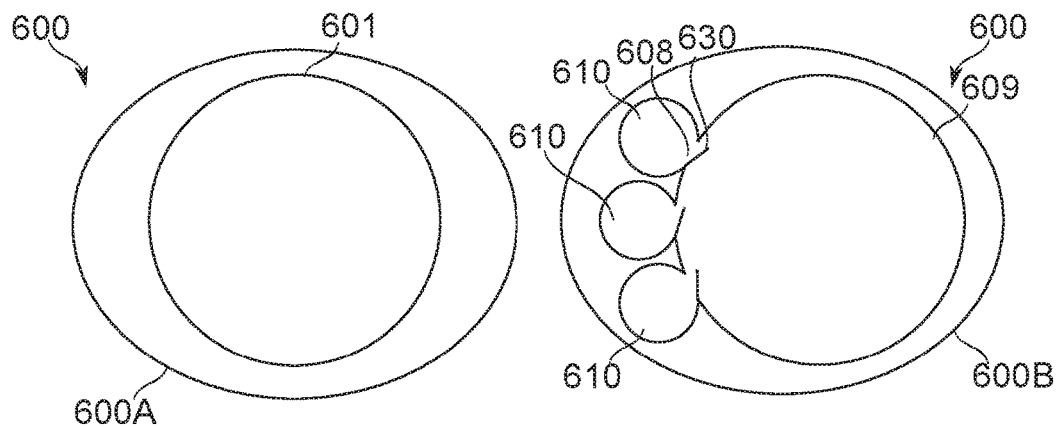
FIG. 6A
FIG. 6B
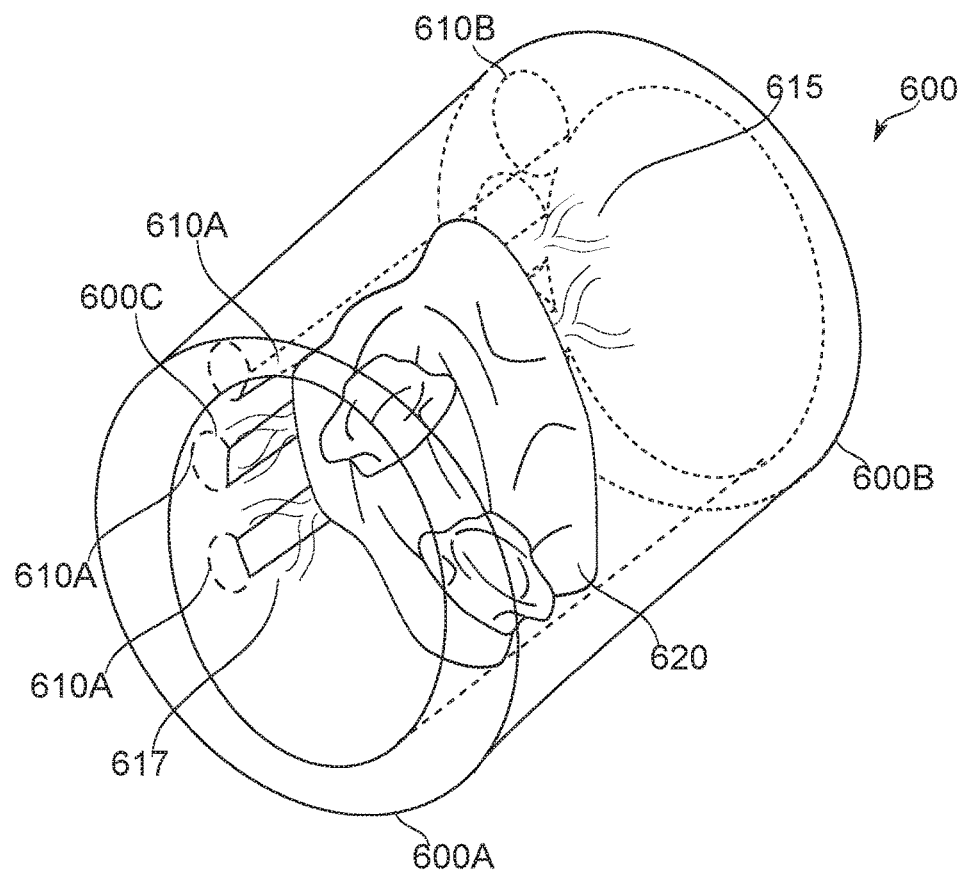
FIG. 6C

CLEANING METHOD FOR PREPLESS COLONOSCOPY

RELATED APPLICATIONS

This application is a National Phase of PCT Patent Application No. PCT/IL2015/050379 having International filing date of Apr. 8, 2015, which claims the benefit of priority under 35 USC § 119(e) of U.S. Provisional Patent Application No. 61/977,173 filed on Apr. 9, 2014. The contents of the above applications are all incorporated by reference as if full set forth herein in their entirety.

FIELD AND BACKGROUND OF THE INVENTION

The present invention, in some embodiments thereof, relates to methods for clearing of fecal matter the wall of a colon or other body lumen for diagnostic inspection, and, more particularly but not exclusively, to methods for such clearing of fecal matter in patients who have undergone no or restricted preparation to reduce and/or remediate the particle structure of colon contents before diagnostic inspection.

Human diet varies according to nationality, age, gender, income, ideology, and more. Digestive flora, which can both help and hinder digestion, also vary between individuals. As much as the mechanical and chemical processing of the gastrointestinal tract to extract nutrients from food tends to homogenize it, some differentiation remains. Some foods are fully degraded by their passage through the digestive tract; others retain some structure, however altered by passage through the gut.

While partially homogenizing food's original structure, gastrointestinal processing also adds new structure; for example, by aggregating digested particles, and by controlling stool water content. As captured by the Bristol Stool Scale, for example, stool is classified of a scale from 7 (completely liquid) to 1 (small hard lumps). Variables affecting the state of fecal aggregation and fluid content, as well as completeness of food digestion, include the frequency of defecation (normally ranging from five times a day to twice a week), and the speed at which food passes through the gastrointestinal tract (10 hours to 4 days is normal). Gut flora and secretions of the digestive tract also become part of the stool.

A colonoscope provides means for optically and/or electronically imaging the colon and its contents, for example, to look for cancerous and/or pre-cancerous polyps. For effective viewing, a common practice before colonoscopy is to clear as much of a colon's contents as possible, sometimes by aggressive changes to diet and/or by administration of purgatives. In some methods of colon observation, imaging occurs while flushing or washing a portion of the colon with an irrigating fluid. Irrigating fluid, fecal matter and/or other colon contents are drawn out of the colon by suction and/or other methods for transporting matter out of the body. The following patent applications relate to the field of endeavor of the current application: U.S. Patent Application 2010/0185056 by Tal Gordon et al.; U.S. Patent Application 2011/0105845 by Tal Gordon et al.; and U.S. Patent Application 2012/0101336 by Yoav Hirsch et al.

SUMMARY OF THE INVENTION

According to an aspect of some embodiments of the present invention, there is provided a method of limited evacuation of fecal matter content from a colon, comprising: introducing fluid to a distal segment of the colon containing the fecal matter; evacuating the introduced fluid from the colon; monitoring the fecal matter content mixed into the evacuated fluid; and reducing the introducing based on a reduction in the monitored mixed fecal matter content; wherein at least 10% of the original colon segment fecal content remains within the colon.

According to some embodiments of the invention, at least 50% of the remaining fecal content comprises particles above a predetermined size.

According to some embodiments of the invention, the evacuating is through at least one intake aperture of an evacuation lumen, the predetermined size is determined by exclusion of the particles from the evacuation lumen, and the predetermined size is smaller than the largest of the at least one intake apertures.

According to some embodiments of the invention, the reducing comprises stopping the introducing.

According to some embodiments of the invention, the fluid is introduced from a fluid outlet positioned within the distal segment, and the fluid outlet is repositioned based on the reduction in the monitored mixed fecal matter content.

According to some embodiments of the invention, the positioning comprises partially retracting the fluid outlet from the colon.

According to some embodiments of the invention, the monitoring comprises monitoring particle content.

According to some embodiments of the invention, the monitoring comprises monitoring a color of the evacuated fluid.

According to some embodiments of the invention, the monitoring comprises optical inspection of the evacuated fluid.

According to some embodiments of the invention, the monitoring comprises visual inspection of the evacuated fluid.

According to some embodiments of the invention, the monitoring comprises automatic inspection of the evacuated fluid.

According to some embodiments of the invention, the colon belongs to a human subject, and the human subject has eaten a full meal within the last 8 hours.

According to some embodiments of the invention, the colon belongs to a human subject, and contains fecal matter volume equivalent to at least 25% of the carried fecal volume in a normal state of diet and alimentary canal operation.

According to an aspect of some embodiments of the present invention, there is provided a channel for evacuating fecal waste from a human colon, comprising: a lumen, sized for insertion of a distal end thereof to a distal end of the colon; the lumen having a lobed cross-section comprising at least a first and second lobe; a passage between the first and second lobes comprising at least one slot narrower than the widest extent of the cross-section of the first lobe; the first lobe having a cross-sectional area at least 4 times larger than the cross-sectional area of the second lobe.

According to some embodiments of the invention, the channel is enclosed by a wall constructed to resist collapse under application of a pressure differential of at least 0.2 Atm lower within the lumen than surrounding pressure.

According to some embodiments of the invention, passage of fluid between the first and second lobe is gated by a one-way valve member extending along the slot.

According to some embodiments of the invention, the valve member comprises a flap which extends to a proximal end of the slot, but terminates at least 1 cm before a distal end of the slot.

According to some embodiments of the invention, the valve member resists passage of fluid into the second lobe under pressure from the first lobe, more than it resists passage of fluid from the second lobe to the first lobe under equivalent reversed pressure.

According to an aspect of some embodiments of the present invention, there is provided a channel for evacuating fecal waste from a human colon comprising: a lumen, sized for insertion of a distal end thereof to a distal end of the colon; wherein external access into the lumen at the distal end of the lumen is through at least one aperture; and the at least one aperture is configurable from among a plurality of different sizes.

According to some embodiments of the invention, the size of the aperture is configurable by adjustment while the lumen is inserted into the colon.

According to some embodiments of the invention, the size of the aperture is configurable by adjustment of pressure at the distal end of the channel.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 6A-6C illustrate sections of an evacuation tube in cross-sections and in partially transparent perspective, the lumen of the tube having a plurality of lobes through which waste and fluid is evacuated.

DESCRIPTION OF SPECIFIC EMBODIMENTS OF THE INVENTION

Figure 1:
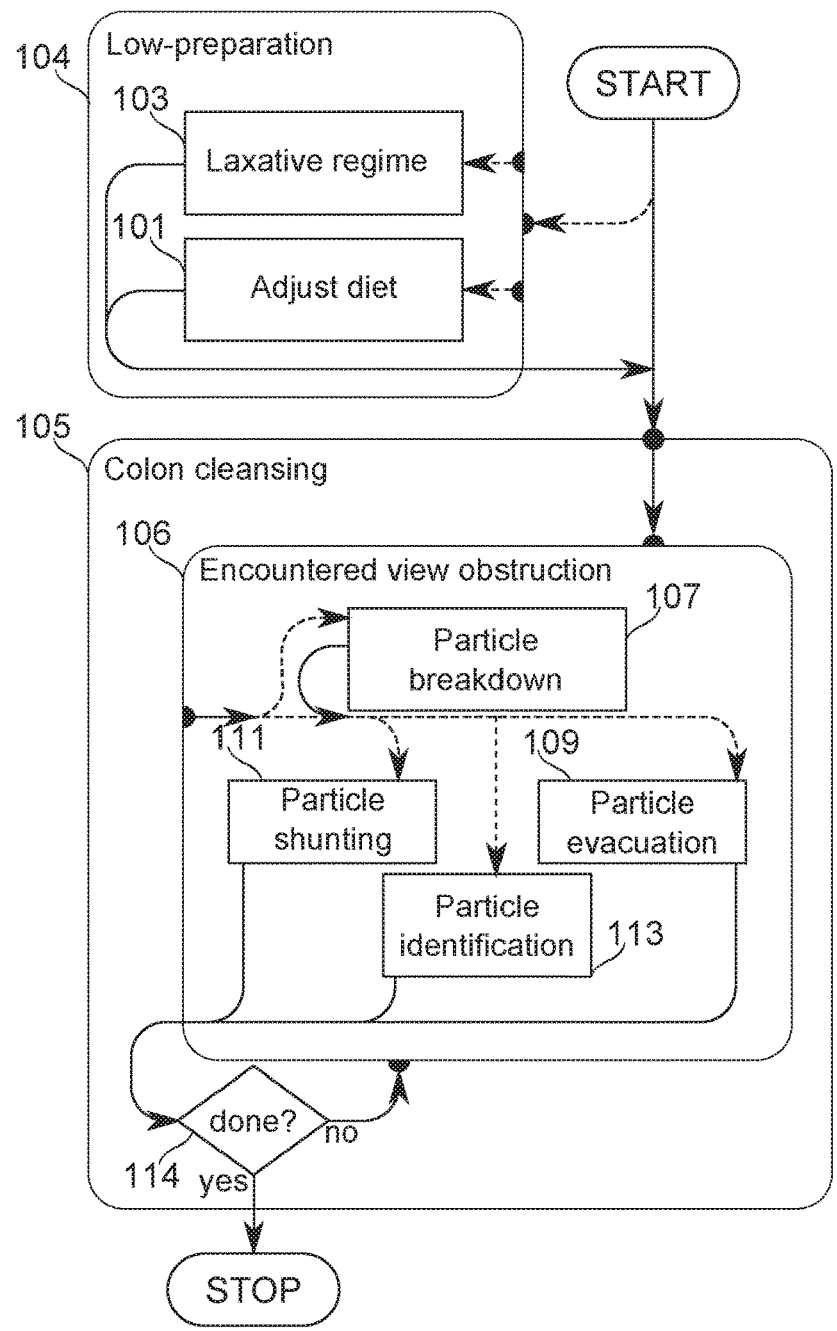
FIG. 1 is a flowchart outlining alternative and/or parallel methods of managing the clearing of various forms of digested and/or partially digested food particles from an intestinal tract, according to some exemplary embodiments of the invention.

The present invention, in some embodiments thereof, relates to methods for clearing of fecal matter the wall of a colon or other body lumen for diagnostic inspection, and, more particularly but not exclusively, to methods for such clearing of fecal matter in patients who have undergone no or restricted preparation to reduce and/or remediate the particle structure of colon contents before diagnostic inspection.

Overview

A broad aspect of some embodiments of the invention relates to cleaning of a colon, and in particular, cleaning of a colon during a colonoscopy procedure before which no or low-intervention colon preparation has been performed.

An aspect of some embodiments of the invention relates to partial clearing of fecal material from selected wall regions to allow diagnostic inspection thereof. In some embodiments of the invention, removal of all fecal matter is deliberately avoided during a no or low-preparation colonoscopy. In some embodiments, larger fecal matter particles are left behind, while smaller particles are cleared. Potentially, this distinction allows a colonoscopy procedure to proceed more quickly, by avoiding a need to fully evacuate waste volume from the colon. In some embodiments, large waste particles which are substantially coherent are optionally moved aside and/or ignored, rather than have effort expended on their further breakdown and/or evacuation. Potentially, this allows examination to proceed even in a colon which is not fully purged of fecal matter.

In some embodiments of the invention, clearing of fecal material is performed segment-by-segment. In some embodiments, a segment is any convenient length of colon, for example, 10-20 cm, 20-40 cm, 40-80 cm, or another range of lengths having the same, intermediate, larger, and/or smaller bounds, up to the length of the whole intestine. In some embodiments, a segment is an anatomically-defined segment of colon, defined, for example, by natural constriction and/or bending of the organ. It is a potential advantage, during colon cleaning, for the unit of current cleaning attention to be an anatomically-defined segment, where natural bending and constriction helps to guide, restrict, and/or contain the movement of fecal matter and/or irrigation fluid. Potentially, such guiding, restricting and/or containing serves to sequester fecal matter which remains within the colon such that it does not interfere with present viewing.

An aspect of some embodiments of the invention relates to monitoring of evacuation results in the determination of colon cleansing progress. In some embodiments, evacuation fluid color (or another optical, chemical, or physical property) changes as colon cleaning in a particular region of the colon nears completion. The most easily broken down and/or evacuated particles are evacuated initially, leading to a high particle load and/or color change in the fluid which is introduced to irrigate and cleanse the colon. As the evacuation fluid more nearly returns to the color and/or other properties of the irrigation fluid, a condition of diminishing returns potentially arises. Waste potentially still resides in the colon segment being cleaned; however, it is waste that for some reason—typically related to size—is more resistant to evacuation. Large waste particles, in some embodiments, are handled by other means than evacuation. For example, they are shunted away from a site of inspection, or simply ignored (as being obviously unimportant for diagnostic determinations). In some embodiments, determination to stop cleaning operations, and/or to stop intensive cleaning operations, is based on determination that evacuated fluid is substantially free of evacuated fecal waste, and/or is notably trending to a lowered state of waste. Optionally, this decision is taken, even while substantial fecal waste (up to 1%, 2%, 3%, 4%, 5%, 10%, 15%, 20%, or another intermediate, larger, or smaller percentage of the original waste volume) remains in the colon. Nevertheless, in some embodiments, at least some larger percentage of the fecal waste is evacuated from the colon; for example, at least 70%, at least 80%, at least 90%, or at least another greater, lesser, and/or intermediate amount of the original waste volume.

In some embodiments of the invention, fecal particles remaining in a colon segment after cleaning remain above a predetermined size. The fraction of remaining particles above the predetermined size is, for example, 20%-40%, 30%-50%, 40%-80%, 50%-90%, 80%-100%, or another range having the same, intermediate, larger, and/or smaller bounds. In some embodiments, for example, the predetermined size is based on the size of particles which can be effectively evacuated through one or more cleaning system evacuation lumens. In some embodiments, the predetermined size is a fraction of the maximum size which can be evacuated, for example, 50%, 70%, 90%, or another larger, smaller, or intermediate fractional size. The maximum size which can be evacuated and/or effectively evacuated, in some embodiments, corresponds, for example, to the dimensions of an intake aperture of an evacuation lumen, and/or the internal dimensions of an evacuation lumen.

An aspect of some embodiments of the invention is the provision of an asymmetrically lobed channel for evacuation of waste. In some embodiments, a primary lobe comprises the largest pathway for waste conduction, capable of handling the largest and/or greatest number of particles of all provided lobes. In some embodiments, a secondary lobe is connected to the primary lobe along a slot. The secondary lobe, although smaller, provides a partial pressure shunt which operates when the primary lobe becomes or begins to become occluded. Potentially, this reduces the degree to which the primary lobe becomes impacted, by relieving suction pressure. In some embodiments, a one-way valve member is provided between the primary and secondary lobes, configured to guide purging pressure through the primary lobe, while allowing suction pressure to shunt away from the primary lobe. Potentially, this allows purging force against a blockage to be stronger than suction force which created it.

An aspect of some embodiments of the invention is the provision of variably sizable apertures leading to an evacuation lumen. Waste particle size potentially affects the degree and/or frequency of evacuation lumen blockage. It is a potential advantage to filter larger particles at the evacuation intake when the conditions of fecal content tend to engender intralumenal blockage, but to maintain a fully open lumen when conditions are less demanding (for example, due to uniformly small particle size). In purging, for example, a tip-blockage is potentially easier to clear than an intralumenal blockage. Potentially and conversely, a fully open evacuation intake allows more rapid evacuation of particles than a filtered intake, so long as intralumenal blockages are relatively rare.

Before explaining at least one embodiment of the invention in detail, it is to be understood that the invention is not necessarily limited in its application to the details of construction and the arrangement of the components and/or methods set forth in the following description and/or illustrated in the drawings. The invention is capable of other embodiments or of being practiced or carried out in various ways.

No- and Low-Preparation Particle Management

Reference is now made to FIG. 1, which is a flowchart outlining alternative and parallel methods of managing the clearing of various forms of digested and/or partially digested food particles from an intestinal tract, according to some exemplary embodiments of the invention.

In the course of clearing fecal material which obscures the walls of a colon, in a procedure performed in parallel with diagnostic viewing (such as colonoscopy), several fecal particle forms are potentially encountered. It is a potential advantage for preparation-free wall clearing strategies to be available, suited to different fecal particle forms, in order to achieve rapid, reliable progress of a colonoscope probe through the colon, while achieving a sufficient level of wall clearing to permit complete diagnostic viewing. Additionally or alternatively, it is a potential advantage to use low-impact colon preparation strategies (low-preparation) which adjust patient diet and/or gastrointestinal processing to reduce the presence of particle types which present difficulties in the speed and/or reliability with which they can be cleared from a colon wall.

When the goal, at each stage of a colonoscopy examination, is simply to see nearby patches of colon wall well enough and for long enough to ensure that no abnormalities go unnoticed, both preparation-free and low-preparation strategies are potentially different in their administration and effects than regimes which are administered (either before a colonoscopy begins, or administered while a colonoscopy is underway) with the intent of completely purging a colon segment of fecal waste particles.

FIG. 1 shows a general overview of how different fecal particle management strategies interact to provide clearance of a colon wall for diagnostic viewing during colonoscopy.

In FIG. 1, task flow arrows leading to optional and/or alternative blocks are shown in dashed lines. Task flow into blocks containing sub-blocks is marked with semicircles protruding outside the block outline, while semicircles protruding inside the block outline show continuation points for task flow to sub-blocks.

At block 101, in some embodiments, instructions for dietary adjustments aimed at solid fecal particle type management are optionally provided to and followed by a patient. At block 103, in some embodiments, a laxative regime appropriate to achieving a targeted fecal particle profile is optionally provided to and followed by a patient. One or both of block 101 and block 103, in some embodiments, are part of an optional "low-preparation" regime 104. Low-preparation strategies potentially serve to reduce fecal mass, without targeting complete cleansing of a colon of all fecal mass. Whether or not fecal mass is reduced, another target of low-preparation strategies, in some embodiments of the invention, is remediation of the structure of the colon's fecal content, and in particular, of the structure of fecal particles. In some embodiments, fecal particles are adjusted by preparation of a colon such that they are more easily cleared from the colon wall during colonoscopy by an appropriately designed colon-cleansing device.

At block 105, in some embodiments of the invention, colon cleansing occurs, simultaneously with a procedure for diagnostic examination of the colon such as colonoscopy (not shown). A goal in a typical colonoscopy exam is to obtain unobstructed and/or unambiguous views of all parts of the colon wall in order to detect abnormalities, and in particular, cancerous and pre-cancerous abnormalities. In a full-preparation colonoscopy, an unobstructed view is ensured by aggressively removing all obstructions prior to the beginning of the exam. In a no- or low-preparation colonoscopy accompanied by use of a colon wall-clearing cleansing device, however, it is possible to remove, move, and/or simply disregard wall-view obstructions due to fecal matter as they are encountered. In general, fecal matter view obstructions, as they are encountered (block 106), are broken down (reduced) at block 107, evacuated from the intestine altogether (evacuated) at block 109, moved away from sites they obstruct (shunted) at block 111, and/or disregarded as diagnostically irrelevant (identified) at block 113. As obstructions to view are encountered, colon cleaning continues, optionally concurrent with colonoscopic examination, until the procedure is complete (block 114).

Exemplary Particle Types

In some embodiments of the invention, strategies for fecal particle clearance from an intestinal wall vary depending on aspects of particle size and/or structure.

Exemplary Particle Sizes

In some embodiments of the invention, management of fecal particle clearing is based in part on the basis of particle size. In some embodiments, particle size comprises three broad categories—coarse, medium, and fine. Particle size categories are based, for example, on their suitability for evacuation through one or more evacuation lumens. An evacuation lumen of a cleaning device is, for example, about 3-6 mm in diameter. An evacuation lumen, in some embodiments, is longitudinally sized so that a distal end thereof is insertable to the distal end of a human colon, while a proximal end thereof remains outside the colon. In an exemplary size categorization scheme:

- A coarse fecal particle is too large to pass into and/or through the evacuation lumen as is (in particular, without further reduction in size). It may, however, block an aperture leading to an evacuation lumen.
- A medium fecal particle is small enough to pass into and through the evacuation lumen as is, but also potentially bulky enough to engender at least a partial blockage of the lumen.
- A fine fecal particle is small enough to pass into and through the evacuation lumen, for example, in fluid suspension, without engendering lumen blockage. It may, however, become involved in an existing blockage.

It should be understood that the foregoing definitions of coarse/medium/fine are relative to a particular configuration of a colon cleaning system. Additionally or alternatively, a colon cleaning system potentially comprises more than one evacuation lumen geometry, such that the size definition of a particle is different with respect to different lumens. For example, a cleansing system, in some embodiments of the invention, comprises two lumens with different inner diameters and/or one or more other dimensions characteristic of the lumen cross-section. Additionally or alternatively, the lumens could be of differing cross-sectional shape, independently chosen, for example, from among the alternatives of round, oval, rectangular, trapezoidal, and/or arcuate. In some embodiments, a single lumen is lobed (configured, for example, as two lumens connected along a slot), optionally with one lobe being larger than the other.

Exemplary Particle Structures

Reference is now made to Table 1, which defines broad categories of fecal particle structure, according to some embodiments of the invention. In some embodiments of the invention, management of fecal particle clearing is based in part on the basis of particle structure. In some embodiments of the invention, structural categories of fecal particle composition comprise a plurality of those listed in Table 1. The categories of Table 1 are indicative, and not limiting; they provide a basis for the understanding of different methods and combinations of methods used to achieve the clearance of fecal waste from a colon wall for diagnostic imaging thereof.

TABLE 1

| PARTICLE STRUCTURE TYPE | DEFINITION |
| --- | --- |
| Fine | Non-blocking particle; small enough that structural detail is unimportant for wall clearance. |
| Membranous | Thin, flexible particle, for example, comprising a piece of fruit or vegetable skin. |
| Granular | Tough, possibly hard, non-elastic particle, for example a seed, or bone or seed fragment. |
| Spongiform | Soft, porous, but resilient particle, for example, eggplant body. |
| Fibrous | Soft particle comprising intertwined insoluble fibers, for example, lignin fibers. |
| Gel | Colloidal mass, comprising, for example, soluble dietary fiber gelled in water. |
| Conglomerate | Shedding (soft) particle comprised of a plurality of any other particle structure type. |
| Concretion | Low-shedding (hard) particle comprised of a plurality of any other particle structure type. |

In some embodiments of the invention, conglomerate particles potentially convert, in the process of colon wall clearing, to smaller and/or simpler particle structures. Some particle structures are relatively immune to breakdown during active wall clearing (for example, by fluid jets). In particular, granular, spongiform, and fibrous structures are potentially resistant to mechanical breakdown. Concretion particles, by definition, are difficult to break down during colon wall clearance, as can happen, for example, due to conversion of a conglomerate mass to a concretion by drying due water absorption during constipation. Gel and membranous particles are relatively susceptible to mechanical breakdown into smaller gel or membrane particles, for example under the impact of jets of fluid and/or fluid-gas, or mechanical grinding. Fine particles include particles which are small enough that their further breakdown is unnecessary for colon wall clearance.

Strategies for Colon Wall Clearance

Reference is now made to Table 2, which lists different size-structure combinations of particle configuration, along with typical no- and/or low-preparation strategies used to clear them from a colon wall during and/or previous to a colonoscopy procedure, according to some exemplary embodiments of the invention.

TABLE 2

| PARTICLE TYPE | TYPICAL No- AND/OR LOW-PREPARATION STRATEGIES |
| --- | --- |
| Coarse-Conglomerate | Reduce |
| Coarse-Concretion | Laxative, Shunt, Identify |
| Coarse-Granular | Shunt, Identify, Diet |
| Coarse-Membranous | Reduce, Shunt, Diet |
| Coarse-Spongiform | Shunt, Diet |

TABLE 2-continued

| PARTICLE TYPE | TYPICAL No- AND/OR LOW-PREPARATION STRATEGIES |
|---|---|
| Coarse-Fibrous | Shunt, Diet |
| Coarse-Gel | Reduce |
| Medium-Granular | Evacuate, Shunt |
| Medium-Membranous | Reduce, Evacuate |
| Medium-Spongiform | Evacuate |
| Medium-Conglomerate | Reduce, Evacuate |
| Medium-Concretion | Evacuate, Shunt |
| Medium-Gel | Reduce, Evacuate |
| Fine | Evacuate |

Particle Types and No-Preparation Strategies for Colon Wall Clearance

Of the strategies listed in Table 2, "Reduce", "Shunt", "Identify", and "Evacuate" are all "prepless" (no-preparation) strategies. In particular, in some embodiments of the invention, they occur as wall-clearing operations during a colonoscopy procedure, potentially without previous preparation of the patient's colon.

Figure 2:
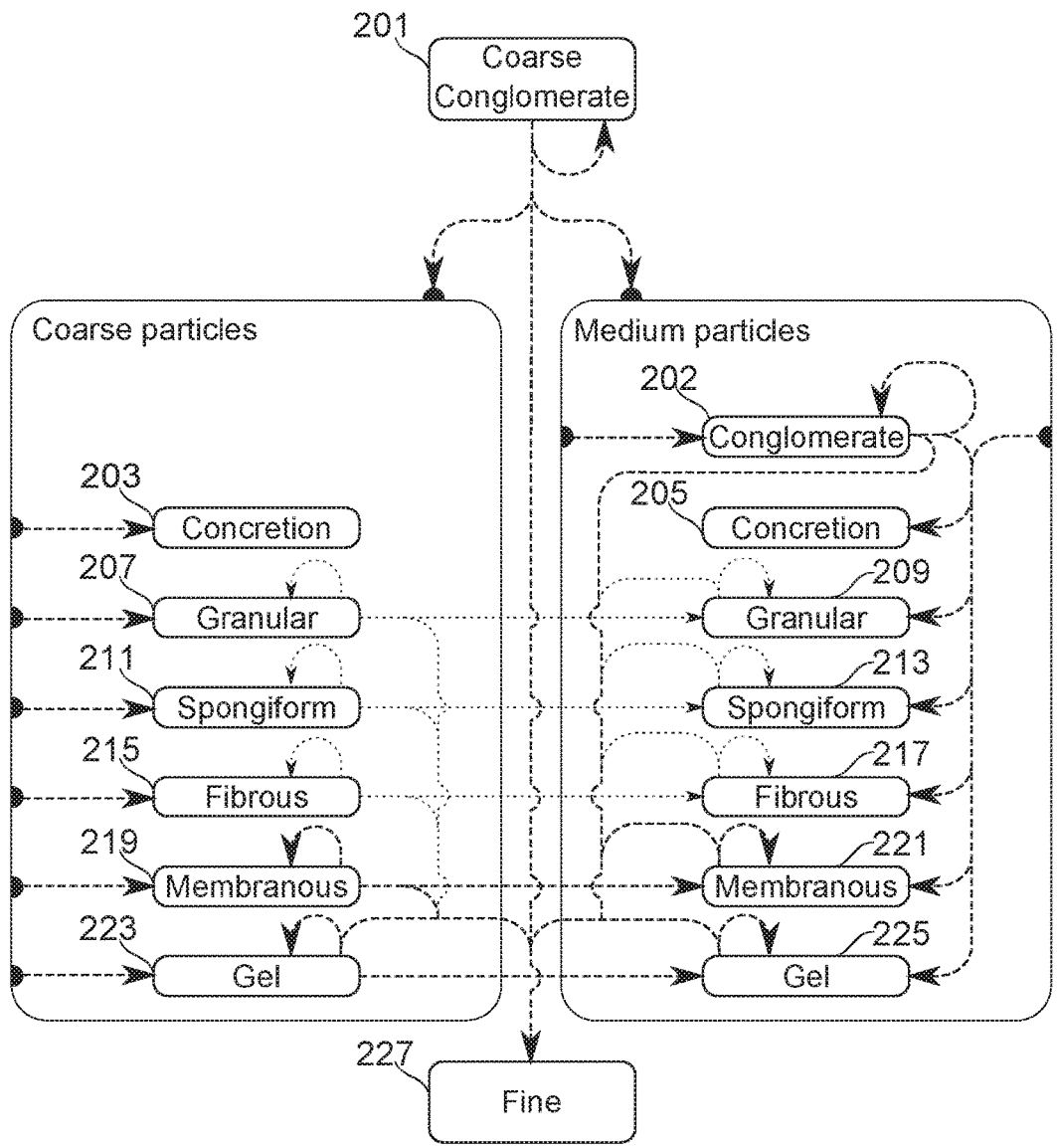
FIG. 2 charts the evolution of fecal particles during colon wall clearance, according to some exemplary embodiments of the invention.

Reference is now made to FIG. 2, which charts the evolution of fecal particles during colon wall clearance. Assertion of a strict taxonomy of fecal particle evolution is not intended by the divisions of FIG. 2; rather, the various types of particles and their properties are described in order to illustrate how different clearing and remediation methods potentially interact with fecal matter in the course of clearing colon walls for diagnostic viewing.

In FIG. 2, particle evolution is shown by dashed arrows leading from source particles to breakdown products. Pathways from particles which are potentially relatively resistant to mechanical breakdown are shown with dotted-line arrows. Flow into blocks ("coarse particles" and "medium particles") containing sub-blocks is marked with semicircles protruding outside the block outline, while semicircles protruding inside the block outline show continuation points for task flow to sub-blocks. Arrows which lead directly to sub-blocks indicate only those sub-blocks. Unconnected crossings are illustrated by semicircular detours.

At block 201, a coarse conglomerate particle is represented. A coarse conglomerate particle potentially ranges from a large fecal mass (a "sausage" or "snake", such as number 3 or 4 in the Bristol stool scale), to a smaller "fluffy" piece (such as a particle in Bristol stool scale 6), to any breakdown piece of fecal matter which remains composite in composition, and too large to pass into and through a colon cleansing device's evacuation lumen. Conglomerate particles consist of a plurality of sub-particles, into which the conglomerate is easily separated. In general, where a particle is "conglomerate" only in that a coarse or medium food particle of another type is coated or impregnated with fine fecal particles, it is convenient to identify it, for the purposes of this discussion, as being of the type of the coarse or medium particle.

A coarse conglomerate particle 201 is potentially reduced, in some embodiments of the invention, by breaking down—for example, under the action of a colon cleaning system—to another type of coarse, medium, or fine particle. Conversely, any other particle is potentially encountered by a colon cleaning system after active or incidental breakdown from a larger (composite or same-type) particle, and/or encountered in its native form. Medium conglomerate particles 202 potentially also break down, for example, under the pressure of cleaning system jets or simply due to partial dissolution in irrigation fluid supplied by a cleaning system. A medium conglomerate particle 202 is potentially drawn into an evacuation lumen for passage therethrough. Within the evacuation lumen, a conglomerate particle potentially breaks down further, for example due to an active grinding mechanism, and/or due to shearing forces inherent in the surrounding fluid within which it is transported. Alternatively, the particle is transported out of the colon as is, or deforms during transportation without breaking apart.

A coarse concretion particle 203 corresponds, for example, to the "hard lumps, like nuts" consistency of a type 1 stool on the Bristol stool scale. By definition, it is too hard to break down further by a colon cleansing system, and thus is an endpoint particle, too large to evacuate. In some embodiments of the invention, such particles are cleared from view by shunting them to another position (for example, "kicking" them sideways, forward, or backward with a jet of fluid, as described hereinbelow). Optionally, a coarse concretion particle is identifiable as irrelevant to diagnosis, and small enough so that it does not comprise a significant blockage of the view of the colon wall. A medium concretion particle 205 is potentially evacuated, but, due to its consistency, also introduces a particular risk for engendering blockage of an evacuation lumen. Management of particles which potentially engender blockages within an evacuation lumen is discussed further hereinbelow.

A coarse granular particle 207 typically but not exclusively corresponds to a large seed or seed portion (such as a legume, kernel of unpopped popcorn, uncooked grain of rice, or another hard piece of ingested material, potentially including an ingested foreign body). While digestion may have weakened the particle so that jetting, shearing, and/or grinding potentially reduces its size, the structural integrity of granular particles in general is too strong to break down under the application of forces appropriate to the delicate operating environment of a colon cleansing system. Like coarse concretions, granular particles are dealt with in some embodiments of the invention by shunting and/or identification (as irrelevant) when encountered. Medium-sized granular particles 209 are small enough to evacuate, but also accompany a particular risk for engendering blockage, since they are relative hard and resistant to fragmentation and/or deformation. As described for coarse concretions, it is a potential advantage to manage the risk of blockage by active sensing and/or purging mechanisms of a colon cleaning system.

Spongiform 211, 213 (for example, eggplant-like) and fibrous 215, 217 ("tangled strings", such as of fibers from bean pods or gristly portions of meat) particles are likewise examples of particle structures resistant to further breaking down by a colon cleansing system. Being relatively soft, the medium versions of these particle structures are potentially easier to draw through an evacuation lumen than granular or concretion particles. However, the coarse soft particles are potentially more liable than harder coarse particles to be deformed by suction and drawn into the intake aperture of an evacuation lumen to become lodged. Such end-plugging presents a somewhat different situation for purging and/or protection of an evacuation lumen than internal lumen plugging, as described hereinbelow.

Some coarse membranous particles 219 are potentially degradable (reducible) into smaller fragments by mechanical action, such as agitation by water jets, mechanical grinding, and/or fluid shear forces within an evacuation lumen. Other coarse membranous particles, particularly those which comprise an ingested foreign body such as a fruit sticker, or a piece of food wrapping, are more difficult to break down further. When a coarse membranous particle reaches an evacuation lumen intake aperture, it is a potential source of blockage, as its shape readily changes to conform to the shape of the intake. Medium membranous particles 221 potentially present very different cross-sections to a flowing stream, so their contribution to blockage development at or within an evacuation tube is potentially likewise variable.

Coarse or medium gel particles 223, 225 comprise colloidal material such as secreted mucous, and/or hydrated soluble or partially soluble dietary fiber. Potentially, accumulations of such material (of any size) are easily broken apart by a colon cleansing system, either outside or inside it. The risk for blockage of an evacuation lumen is primarily due to the viscosity of inspired material as it passes through an evacuation lumen. Mucosal material in particular potentially occurs along the lining of a colon wall with sufficient transparency that it does not need to be dislodged in order for diagnostic viewing to occur.

Fine particles 227 potentially comprise bacterial particles, and/or small fragments of food of any original structure broken off in the course of digestion. From the point of view of the mechanics of fecal waste particle evacuation, fine particles of any structure are roughly equivalent. By the definitions used herein, all such particles are susceptible to removal from the colon by evacuation. In some cases, fine particles re-agglomerate to each other and/or to larger particles (not shown).

Reducing Particles

Figure 3:
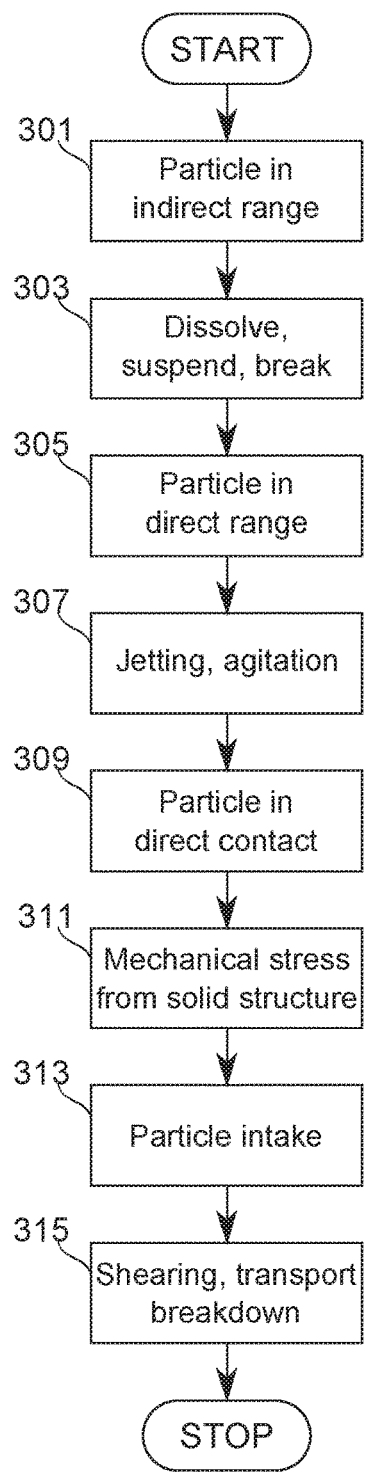
FIG. 3 is a flowchart describing the reduction of fecal particles by a colon wall cleansing system, according to some exemplary embodiments of the invention.

Reference is now made to FIG. 3, which is a flowchart describing the reduction of fecal particles by a colon wall cleansing system, according to some exemplary embodiments of the invention.

At block 301, in some embodiments, a fecal particle comes within the indirect range of influence of a colon cleaning system. The indirect range of influence is considered as the range at which fecal matter is influenced by undirected actions (or the side-effects of directed actions) such as the introduction of fluid to the colon by an irrigation system (which reaches the particle), and/or the insufflation of the colon, which potentially moves the colon wall such that portions of fecal mass separate from it and/or each other.

At block 303, in some embodiments, a fecal particle, typically a conglomerate particle, is reduced in size by breakage of a fecal mass under changing conditions of colon volume, and/or by at least partial dissolution in a pool of irrigating fluid which reaches to the fecal particle.

At block 305, in some embodiments, a fecal particle comes within the direct range of a colon cleaning system. In some embodiments of the invention, a colon cleaning system is capable of producing irrigating jets which introduce pressurized streams of fluid and/or gas into the bowel, allowing targeted erosion of fecal masses from a distance. Additionally or alternatively, the jets comprise a general (potentially untargeted) spraying of mechanically energetic fluid particles and/or gas pockets around a region of the bowel. Potentially, fluid which has built up within the colon is agitated by irrigation and/or evacuation currents.

At block 307, in some embodiments, fecal particles within the direct range of the colon cleaning system are reduced in size. Potentially, irrigation jets impinge on clumps of fecal material, breaking them into smaller portions. In some embodiments, gas added to a fluid jet potentially aids the process of breaking a particle apart by introducing turbulence, which continuously redirects the energy of the jet such that it is more likely to encounter points of structural weakness to help break clumps apart. Potentially, the gas itself is alternately compressed and expanded by the variable forces of the jet, allowing it to act to break apart particles partially by entering crevices of the particle under compression, then expanding from within. Circulating fluid potentially washes over fecal particles, speeding their dissolution. In addition to the destruction of conglomerate particles, jets, circulation, and other active mechanical energy potentially act to break apart membranous particles, for example, those which are prone to tearing.

At block 309, in some embodiments, fecal particles come into direct contact with the colon cleaning system and/or colonoscope itself. In some embodiments, contact is encouraged by suction pressure from an evacuation lumen. In some embodiments, the colon cleaning system comprises a grating or other protective structure. In some embodiments, the lip of the lumen itself is directly encountered. In some embodiments, a penetrating and/or grinding tool (for example, a wire spring or brush pushed out from a working channel of the colonoscope) is guidable into a fecal mass, and/or is positioned (for example, near an evacuation lumen) such that fecal particles are drawn into its range. In some embodiments, a lateral side of a colonoscope or cleaning system tube presses against fecal matter, and/or agitates a "soup" of fecal matter by its passage.

At block 311, in some embodiments, fecal particles potentially break apart due to direct contact with structures of the cleaning system. For example, particles being sucked toward an evacuation lumen are potentially broken apart upon encountering a lumen guard structure, such as a grid. Additionally or alternatively, particles which reach an aperture leading into the evacuation lumen itself are potentially torn apart by the pressure differential they encounter there. In some embodiments, a particle reducing tool (such as a wire or spring protrusion) is positioned to encounter fecal masses, potentially breaking them apart. In some embodiments, the penetrating tool is actively energized, for example, to vibrate, rotate, reciprocate, thrash, or otherwise move such that fecal particles tend to break apart when they encounter it. In some embodiments, the sides of a colon cleansing system and/or colonoscope are usable to assist in breaking apart fecal matter. For example, the distal end of the colonoscope and/or cleansing system probe is potentially passed into a fecal mass, breaking it apart by its distal/proximal motions, and/or by motions of rotation. Such breakage is potentially aided by providing the probe with a non-circular cross-section, and/or by feces-breaking irregularities provided along the length of the probe. Potentially, fecal matter over which the probe runs is broken apart and/or smeared by the shearing force of the passage itself.

At block 313, in some embodiments, fecal particles enter the cleaning apparatus itself. Within the apparatus, there are, in some embodiments, passive and/or active structures for further breaking apart particles. In some embodiments, particles are subjectable, optionally under automatic control, to changes of pressure in an evacuation lumen of the cleansing device. In some embodiments, changes of the evacuation lumen contents are made—for example, as gas/fluid mix is deliberately introduced to the evacuation lumen, for example, to enhance turbulence.

At block 315, in some embodiments, fecal particles are reduced in size within the cleaning apparatus itself. In some embodiments of the invention, reduction of the particle comprises a breaking interaction with an energized grinding, graining, or other structure, for example a rotating, reciprocating, or vibrating spring, auger, tube, or other member. In some embodiments, reduction of the particle comprises breaking encounters with irregularities within an evacuation lumen, for example, encounters with lumenal wall ridges, bumps, and/or constrictions, and/or another structure within the lumen, for example, a wire or roughened aperture. In some embodiments, reduction of the particle comprises breaking encounters with turbulence in an evacuation lumen engendered by such an irregularity.

In some embodiments of the invention, reduction of fecal particles occurs due to shearing forces within the fluid flow of an evacuation lumen. In some embodiments, evacuation pressure is varied, and this variation in evacuation pressure leads to forces acting on the fecal particles, which potentially breaks them apart. The variation in evacuation pressure is optionally generated in response to sensed changes in evacuation lumen conditions (for example, pressure), which potentially correspond to developing and/or existing blockage conditions. In some embodiments, applied pressure and/or pressure changes are sufficient to create cavitation, which potentially acts to disrupt the structure of fecal particles. In some embodiments, a ratio of fluid/air mix is altered, potentially creating turbulence and/or compression breaking effects, for example, similar to those described with respect to fluid jets hereinabove. It should be noted that these actions, potentially leading to particle reduction, potentially at least partially overlap with actions to evacuate a particle, as described hereinbelow.

Shunting Particles

Figure 4:
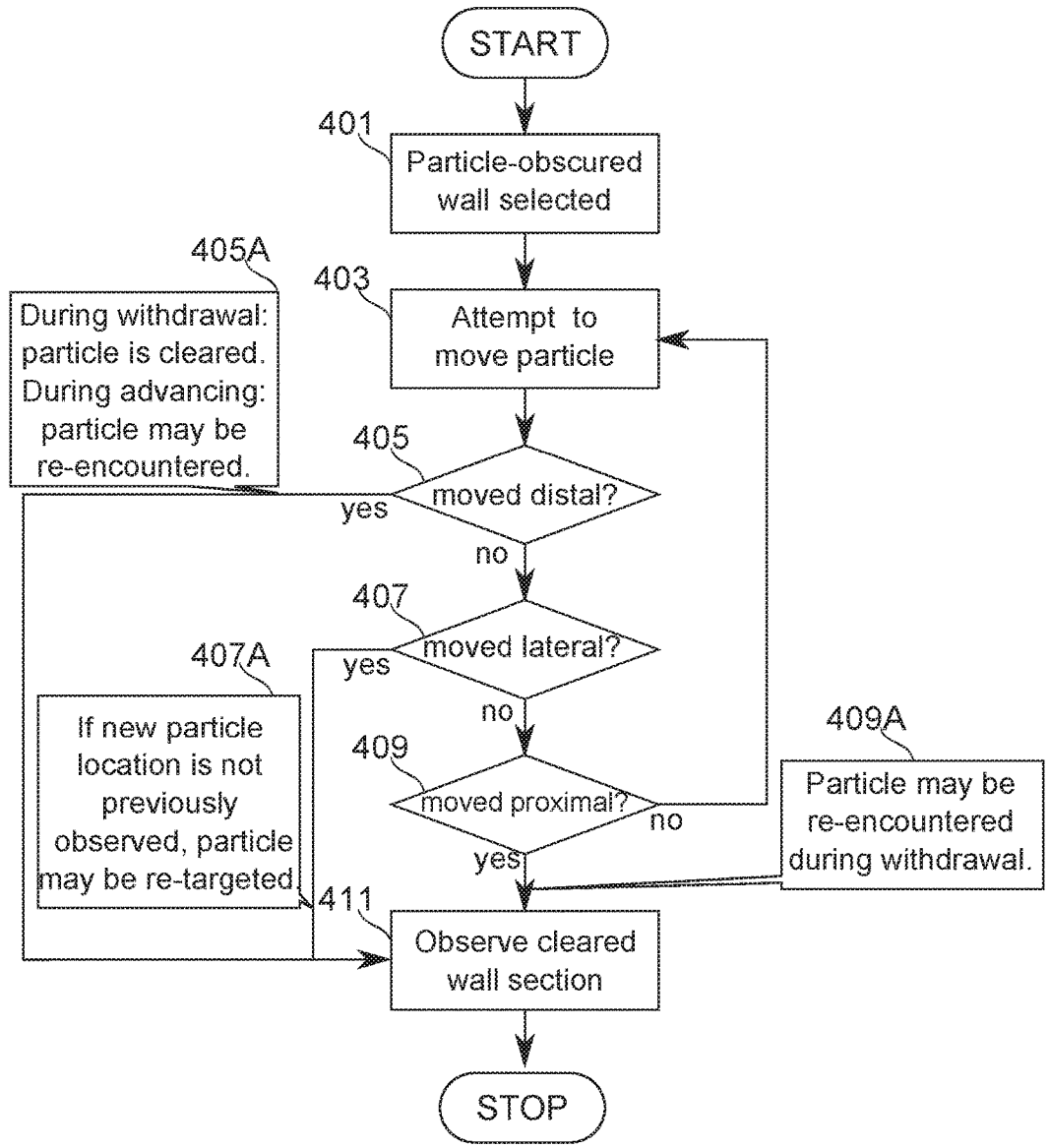
FIG. 4 is a flowchart schematically describing shunting of fecal particles for clearance of a colon wall for diagnostic observation, according to some exemplary embodiments of the invention.

Reference is now made to FIG. 4, which is a flowchart schematically describing shunting of fecal particles for clearance of a colon wall for diagnostic observation, according to some exemplary embodiments of the invention.

The flowchart begins, and at block 401, in some embodiments, a region of colon wall is at least partially obscured from viewing by a fecal particle of sufficient size that it potentially interferes with forming a definite diagnostic opinion about the presence of a colon wall abnormality such as a polyp. Alternatively, the particle is targeted for removal from its position for another reason, for example, as an irritant preventing an overall clear view of a target region. Potentially, the fecal particle is too large to evacuate, and/or too strongly constructed to be broken apart for evacuation.

At block 403, in some embodiments, a fluid jet, fluid/gas jet, or another mechanical disturbance capable of reaching the particle is deployed, optionally aimed at the particle. Additionally or alternatively, the mechanical energy which is deployed (for example, by one of the means described hereinabove with respect to particle size reduction) affects a general area comprising the position of the target particle.

The outcome with respect to the particle at this point is variable, depending on conditions at the point of activity. At block 405, in some embodiments, the particle is "kicked forward" distally into the colon by impinging force, for example, the force of a spray jet. Distal motion of the particle is potentially to another place in the current view, to a distal position within the same colon segment, and/or distally into another colon segment. Callout block 405A describes potential consequences of this case. If block 403 occurs while a colonoscope is being withdrawn from a colon, distal displacement of a fecal particle is potentially sufficient to prevent the particle from interfering with the remainder of a colonoscopy procedure. If block 403 occurs during a phase of advancement of a colonoscope distally into a colon, potentially, the particle may be encountered again during further advancement, and is again susceptible to being moved around. With the previously blocked region of wall exposed, the flowchart continues at block 411.

Additionally or alternatively, at block 407, in some embodiments, the particle remains in view, but is knocked to the side, where it now covers a position which was previously viewable. Callout block 407A mentions potential consequences of this case. When the newly blocked position of the particle was already observed to be clear, there is no particular need to continue operations to cleanse the colon wall of this particle. If not previously observed, the particle may be re-targeted when the unobserved region is selected for viewing.

At block 409, in some embodiments, the particle ends up behind (proximal to) the area of viewing. This can happen, for example, if the drainage of irrigation fluid from a fluid jet reflects back from a distal portion of colon wall to drain into a proximally located region of colon, potentially carrying the target particle along with it. Callout block 409A mentions potential consequences of this case. Potentially, the particle will be encountered again during withdrawal of the colonoscope, in which case, the shunting procedure is optionally carried out again. At this stage, however, the particle is at least temporarily of no concern, and the flowchart continues at block 411.

If the particle has not moved, the flowchart returns to 403 to attempt to move the fecal cover for the selected wall region again.

At block 411, the cleared section of wall is observed, for example, to make a diagnostic determination as to the presence or absence of a polyp, and the flowchart ends.

In some embodiments of the invention, some large particles are optionally withdrawn from the colon by a secondary evacuation lumen. One potential limitation on the diameter of a colon cleansing system lumen diameter is its effect on the navigability of a colonoscope probe to which it is attached. A relatively less-navigable but large-diameter secondary evacuation lumen, however, potentially allows more rapid and/or reliable removal of large-particle waste that reaches relatively proximal positions in the colon, such as the rectum. Thus, in some embodiments, a larger-diameter evacuation lumen is optionally inserted to a relatively short distance within a proximal colon segment, such that coarse material that reaches the proximal segment is readily drained. In some embodiments of the invention, the lumenal diameter is, for example, 5-8 mm, 6-10 mm, 8-12 mm, or another range of diameters having the same, intermediate larger, and/or smaller bounds.

Evacuating Particles

Figure 5:
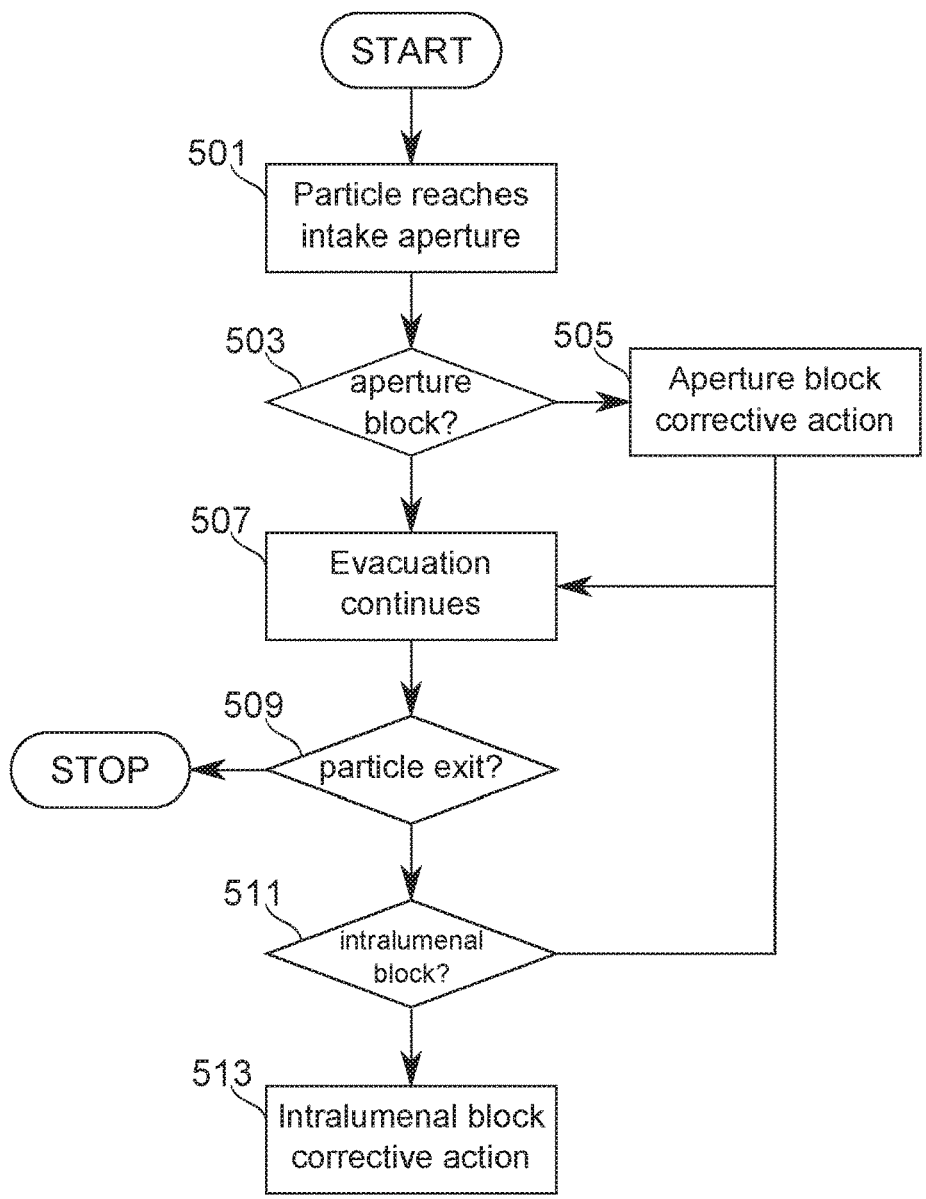
FIG. 5 is a flowchart summarizing operations to remove fecal particles from a body lumen (for example, a colon) by evacuation, according to some exemplary embodiments of the invention.

Reference is now made to FIG. 5, which is a flowchart summarizing operations to remove fecal particles from a body lumen (for example, a colon) by evacuation, according to some exemplary embodiments of the invention. The flowchart describes operations from the notional viewpoint of a particular fecal particle, but it is to be understood that evacuation comprises a continuous process during an examination, of which the various blocks described are potentially recurring way-points.

At block 501, in some embodiments, a particle is pulled to the distal aperture of an evacuation lumen. For the sake of illustration, the particle is treated in the following descriptions as a "medium" sized particle, that is, as a particle which can pass through the evacuation lumen, but also potentially can engender a blockage of the lumen.

At block 503, in some embodiments, a determination is made as to whether or not a distal aperture blockage of the evacuation lumen is developing, and/or has occurred. Determination of the blockage potentially comprises a change in pressure at a particular point at or near the distal aperture, and/or another sensed parameter, such as a rate of flow or change thereof, optical motion detection or a change thereof, detection of a drop in light reaching a sensor (for example, due to physical shadowing by a particle), and/or any other method capable of detecting an existing and/or developing blockage condition.

As for other determinations described with this flowchart, it should be understood that this determination is potentially recurrent, with or without the presence of a particle at the distal aperture, or any other particular place.

At block 505, in some embodiments, action is taken to correct an intake aperture blockage-related condition. In some embodiments, the action comprises, for example, a reduction, cessation, and/or reversal of evacuation pressure. Additionally or alternatively, the action comprises deployment of another means of destroying and/or dislodging a blockage, such as a jet positioned to clear the intake aperture, a device for mechanically poking through the intake aperture, or another method of removing material from an intake aperture.

At block 507, in some embodiments, evacuation of the particle through the evacuation lumen continues.

At block 509, in some embodiments, if the particle has exited the proximal side of the evacuation lumen, the flowchart ends.

Otherwise, at block 511, in some embodiments, a determination is made as to whether or not an intralumenal blockage of the evacuation lumen is developing and/or has occurred. In some embodiments, this determination is conflated with the determination of a distal aperture blockage. In some embodiments, the provision of sensing means for conditions within the evacuation lumen is sufficient to allow distinguishing between an aperture blockage and an intralumenal blockage. In some embodiments, two or more different sections of an evacuation lumen are separately monitored, such that a more proximal blockage is distinguishable from a more distal blockage.

If no blockage condition is determined to exist, the flowchart returns, in some embodiments, to block 507. Otherwise, a blockage and/or developing blockage is determined to exist, and at block 513, in some embodiments, an action is taken to correct the condition. In some embodiments, the action taken comprises, for example (as in block 505), a reduction, cessation, and/or reversal of evacuation pressure. Optionally, the duration, strength and/or number of cycles with which the evacuation pressure change occurs is determined based on the location at which the blockage condition is determined to exist (for example, an aperture blockage condition response potentially comprises a single strong reversal to "blow off" the blockage, while an intralumenal blockage condition response potentially comprises a number of rapid cycles of negative and positive pressure that "hammer" the blockage in an attempt to both dislodge it, and reduce the likelihood of the blockage reoccurring once full evacuation continues). The flowchart returns to block 507.

Reference is now made to FIGS. 6A-6C, which illustrate sections of an evacuation tube 600 at cross-sections 600A, 600B, and in partially transparent perspective, the lumen of the tube having a plurality of lobes 609, 610 through which waste and fluid is evacuated.

In some embodiments, intralumenal blockage conditions are limited by a lobed evacuation lumen geometry, comprising a first lobe 609, and one or more auxiliary lobes 610. In some embodiments, lobes are of different sizes, such that a larger primary lobe 609 and one or more smaller auxiliary lobes 610 are defined. In some embodiments of the invention, an auxiliary lobe 610 is in fluid communication with a first lobe 609 along a slot-like connecting region 608. In some embodiments, fluid access to the auxiliary lobe is only through the slot 608 (that is, the second lobe lacks an externally exposed intake aperture corresponding to external aperture 601 of lobe 609). The slot-like entrance to the second lobe is potentially relatively difficult to completely block, due to its extended nature, such that free fluid entry into and through it from the first lobe 609 is potentially maintained as long as the second lobe 610 itself remains unclogged. Furthermore, the slot is configured, in some embodiments, such that particle sizes capable of entering the second lobe are of a particularly small size in at least one dimension relative to the lobe lumen dimensions, further reducing the risk of clogging.

In some embodiments, a valve member, for example, a flexible flap 630, extends across and along the slot leading between a primary lumen lobe and an auxiliary lumen lobe. In some embodiments, the valve flap 630 terminates before reaching the distal end of the lumen, for example, 1 cm, 2 cm, 5 cm, 10 cm, or another longer, shorter, or intermediate distance. When pressure exerted in a primary lobe is higher than in the auxiliary lobe, the flap 630 (when located with a free end substantially within the primary lumen lobe) tends to close, forcing flow into the primary lobe. When pressure is approximately equal or lower in the primary lobe, the flap 630 tends to open. Potentially, this allows force to be generated in a distal direction from a proximally-located pressure source, which concentrates pressure and/or flow against an existing and/or developing blockage of the primary lobe—up to the distal terminus of the valve flap 630. In the case of suction, however, the open end of the valve provides an inlet that somewhat equalizes pressures in the primary and auxiliary lobes. Thus, the auxiliary lobe potentially provides more effective shunting of suction pressure than of purging pressure. Potentially, this helps to ensure that the distally-acting force available to purge a block remains higher than the suction force that originally impacted it.

FIG. 6C illustrates an exemplary condition where a portion of evacuation lumen 610 is nearly blocked by plug 620 of waste particles. Auxiliary channels 610 are shown extending from their distal-most cross-sections 610A (in a plane 600C transverse to the channel axis), to more proximal cross-sections 610B in transverse sectional plane 600B. In some embodiments of the invention, the channels are variable in cross-section along their length. For example, as shown, channel 609 is centered in the body of the evacuation tube 600 at its distal aperture 601, but offsets along the evacuation channel, allowing auxiliary channels 610 to assume larger diameters within the evacuation tube wall.

In some embodiments, auxiliary channels 610 (away from slot 608) are circular in cross-section, as shown. In some embodiments, auxiliary channels 610 comprise grooves, and lack a widening beyond slot 608 along all or a portion of their length. In some embodiments, auxiliary channels 610 narrow monotonically beyond slot 608. Potentially, this reduces clogging by giving entering particles no anchoring neck in which to lodge. In some embodiments, auxiliary channels are relatively large and fewer, for example, 1, 2, 3, 4 or more distinct channels, each having cross-sectional areas of 5%, 10%, 15%, 25%, or another larger, smaller, or intermediate relative area of the largest lobe. Such larger channels potentially allow continued evacuation of fine particles past a blockage. In some embodiments, a larger number of smaller channels is provided, for example, 10, 20, 50, 100, or another greater, larger or intermediate any number of grooves around the circumference of a main channel. Potentially, such smaller channels provide sufficient cross-section for pressure relief even if the main channel is blocked, while also being too numerous and/or restricted in particle access to become entirely blocked themselves.

A potential advantage of an auxiliary lobe 610 is as a pressure relief for the first lobe 609. In an exemplary scenario, a large particle 620 passing along the first lobe 609 jams at some point, such as at a partial kinking or constriction of the lumen. In the exemplary scenario, this largely blocks passage of fluid and other particles through the main lobe of the evacuation lumen. Potentially, other particles build up behind the jam, further closing off the lumen. As a result, a pressure differential potentially arises, which tends to pull the blocking particle 620 further into whatever irregularity stopped its motion, and potentially making the jam harder to remedy. However, the auxiliary lobe 610 acts, in some embodiments, as a pressure release, as well as an alternative pathway for flow 617, 615, helping to reduce the tendency of continuing suction to jam the blocking particle further and further. Nevertheless, there is potentially some change in pressure conditions (for example, due to the reduced cross-section through which flow can occur at the position of the blockage). In some embodiments of the invention, this change in pressure conditions is sensed, and an active purging mechanism (such as a reversal of evacuation flow) used to dislodge the blockage. A potential advantage of an auxiliary lumen in this scenario is that a developing blockage is prevented from becoming an impacted blockage, allowing corrective action a greater chance for success. Another potential advantage of auxiliary channels is to allow ongoing erosion by flow along the sides of a main blockage, which would otherwise be protected by the walls of the evacuation lumen.

It should be noted that, in some embodiments where an evacuation lumen operates by the application of suction from an end, the evacuation lumen is designed to withstand at least the differential of the evacuation pressure and the external pressure without collapsing. The withstood differential is, for example, 0.1-0.2 Atm, 0.15-0.4 Atm, 0.2-0.5 Atm, or another range of pressures having the same, intermediate, larger, and/or smaller range limits.

Identifying Particles

In some embodiments of the invention, another "no-preparation" strategy for dealing with fecal waste particles is characterizable as "informed neglect". A particle which clearly identifies as a fecal waste particle—for example, by its size, shape, or color, by the fact that it has been noted to move during irrigation operations, or by another sign apparent to an experienced operator, potentially need not be cleared from the wall at all. This generally supposes that the particle is not large enough to hide a polyp or other abnormality of interest, and/or that it is found located in a position which has previously been determined to be clear of abnormalities.

It should be noted that the practical usefulness of informed neglect as a strategy for dealing with residual fecal matter potentially derives in part from supplying a colonoscope operator with sufficient wall-clearing capacity during an examination to be confident of resolving uncertainty by one or more of the other wall-clearance strategies as necessary. Without this confidence, it is more likely that an operator will find it necessary, as a matter of due caution, to begin with an "overly clean" colon wall, to reduce the chances of a marginal situation arising during a diagnostic procedure.

From another perspective, a colon wall cleansing device can be viewed, in some embodiments, as providing a colonoscope operator with an additional means of interacting with the organ being diagnosed. By providing enhanced options for moving material around in the colon (potentially including evacuation, but not limited to it), a cleansing device creates additional degrees of freedom which allow an operator to more confidently assess what the colonoscope probe encounters.

Low-Preparation Strategies for Colon Wall Clearance

In some embodiments of the invention, a mix of typical no- or low-preparation strategies for handling each type of particle (by size and by structure) is applied to achieve a balance of reduced intrusiveness and/or inconvenience of the pre-colonoscopy routine which a patient undertakes, with the success, speed, and/or convenience of the colonoscopy procedure itself. As a point of reference, full-preparation pre-colonoscopy cleansing typically comprises elements such as conversion of a patient's diet to an aggressively low-residue (low-fiber and/or clear-liquid) diet and/or administration of laxatives sufficiently in advance of a procedure and in sufficient strength to empty the colon of solid matter. The anticipated result of a full-preparation regime is nearly complete removal of solid fecal material from the colon before a colonoscopy procedure begins.

As used in Table 2, however, "Diet" strategies are not primarily aimed at full removal of solid waste from a colon. Instead, "Diet" strategies comprise at least one of a number of different targeted dietary alterations. Such strategies are potentially considered as low-preparation adjustments to a patient's food intake. In general, low-preparation diet strategies comprise one or both of removing food sources of a particular particle structure from a patient's diet, and/or ensuring that foods which have a particular particle structure are reduced to a smaller particle size before ingestion, and/or during digestion.

Similarly, a "Laxative" strategy, in Table 2, comprises laxative administration with the primary aim of improving the performance of wall cleansing operations during a colonoscopy. This is in contrast to full-preparation administration of laxatives, where the target is prior removal from the colon of all or nearly all solid waste as such. In some embodiments, the administration of laxatives in a low-preparation scenario is aimed, not at fully cleansing the colon of solid waste, but rather at softening particles, reducing their size, and/or only partially reducing their volume from that of, for example, a full-bowel situation.

Dietary Adjustments

Reference is now made to Table 3, which lists low-preparation dietary adjustments for different food types, according to some exemplary embodiments of the invention.

TABLE 3

| ACTIONS | GENERAL TYPE OF FOOD | EXAMPLES OF FOOD |
| --- | --- | --- |
| Avoid, Blend, Peel | Digestion-resistant peals or sheaths | whole soft corn kernels, tomato, peppers, potato |
| Avoid, Blend | Digestion-resistant sheaths | onion |
| Avoid | Insoluble fibrous masses | whole legume pods, gristly meat |
| Avoid, Juice | Insoluble fibrous masses | whole citrus fruit |
| Avoid, De-seed | Whole seeds in separable pulp | citrus fruit, watermelon, pepper, cucumber |
| Avoid, Juice | Whole seeds in juiceable pulp | citrus fruit, pomegranate |
| Avoid | Hard seed parts | nuts, sunflower seeds |
| Avoid, Cook | Firm/crunchy fruits and/or vegetables | apple, potato, carrot |

Table 3 lists several types and examples of foods which potentially yield particles resistant to active clearance from a colon through a narrow evacuation lumen, in some embodiments of the invention, together with methods of treating the foods such that the likelihood of such particles being consumed is reduced. Although any food listed can simply be avoided, several of the foods described are potentially made innocuous by one or more basic food preparation techniques—in many cases, techniques which are commonly applied to the particular food type in ordinary cooking. The result makes available a pre-examination which is nearly a normal diet.

Not on the list of Table 3, but also potentially available for a pre-examination diet are so-called low-residue foods, such as those recommended for sufferers of inflammatory bowel disease. Such foods include, for example, those comprising refined or naturally pure grain starch (white rice, white wheat flour), soft fruits and vegetables that are always eaten without peel or seeds (bananas, avocados), milk products, meat (if lean, tender and soft), eggs, and many types of condiments, desserts, and drinks.

Some particles, in particular colloidal fecal masses designated herein as "gel" particles are potentially reconstituted from smaller ingested particles, for example, by colloidal suspension of dietary fiber during the processes of digestion. While colloidal masses of feces are potentially susceptible to breaking apart by forces supplied by a colon cleaning system, it is a potential advantage of some embodiments of the invention to reduce the total fecal volume comprising dietary fiber by reducing dietary fiber in the diet in the period before a colonoscopy exam. Several of the items listed hereinabove in connection with a low-residue diet, particularly those which are not fruits or vegetables, are low in dietary fiber.

Nevertheless, low fiber diets potentially lead to hardening of stool, offsetting, and potentially negating, gains due to fecal volume reduction. It is a potential advantage of some embodiments of the present invention to undertake a pre-exam diet with an appropriate balance of fibrous and low-residue foods, such that a patient reaches an examination table with a balance of fecal matter that is soft (for easy cleansing), with fecal volume such that a moderate (that is, typically achievable using a colon cleaning system) rate of fecal matter evacuation is sufficient to clear colon walls for viewing without adding undue delay to an examination procedure. In some embodiments of the invention, optionally depending on an initial state of a patient's digestive tract, increased consumption of dietary fiber is even encouraged.

For additional assurance of low particle sizes, instructions for a low-preparation diet can include eating nothing that has not been thoroughly mashed or blended, for example a potato puree, a fruit shake, or a tomato sauce. In some embodiments, even something as simple as paying extra attention to chewing in the day or two before an examination potentially provides a benefit for the procedure.

In contrast to a purging diet used in preparation for a full-preparation colonoscopy, the emphasis of a low-preparation diet is on managing the consistency of fecal matter and/or its volume. Excessive fecal volume is only preferably avoided, to avoid delays during examination. Management of particle size is preferable—potentially at a higher priority than volume reduction—to reduce the risk that a cleansing system blockage will make it difficult to complete the exam. Even particles too tough and coarse to evacuate from the colon are potentially dealt with by strategies available at the time of a colonoscopy exam (for example, shunting of the particle), making total particle management by diet optional in some embodiments. In some embodiments of the present invention, the occurrence of particles which cannot be evacuated is reduced by diet to a dependably manageable number for a successful endoscopic imaging session. A manageable average number of coarse, irreducible particles per 10 cm of colon advancement is, for example, 0.5-1, 1-2, 2-4, 4-10, 8-20, or another range having the same, intermediate, larger or smaller bounds. In some embodiments, the number of coarse particles present in the colon during a colonoscopy examination is reduced by diet to zero particles, optionally without clearance of all fecal volume, without the reduction of fecal volume, and/or with an expected increase in fecal volume. In some embodiments, average fecal volume remaining in a colon per 10 cm of colon length is, for example, 1-5 $cm^3$, 3-10 $cm^3$, 5-15 $cm^3$, or another range of fecal volumes per 10 cm of colon length having the same, intermediate, larger or smaller bounds.

Laxatives

In some embodiments of the invention, administration of a laxative is used to prepare a colon for observation. It is, however, a potential advantage for the laxative dose to be matched to the requirements of effective evacuation and/or wall cleansing during a cleansing-system equipped colonoscopy session, rather than to the requirements of an examination which begins from an initially clean colon.

For example, in some embodiments of the invention, a Bristol stool score is determined for the patient one or two days in advance of a planned procedure. Additionally or alternatively, the daily defecation rate of the patient is determined, and/or the rate of passage of a mark food through the gut is determined. Based on the assessment of the current functional state of the patient's digestive tract, laxative is optionally prescribed, in some embodiments, such that a particular stool state can be depended on at the time of the examination itself. For example, a laxative dosage for a patient with a Bristol type 1 or 2 stool can be calculated to ensure a stool state score no lower than 3 or 4 at the time of the exam. It should be understood than any appropriate relationship between current stool score state and target stool score state can be chosen; a minimum target stool score of 5, 6, or even 7 is alternatively chosen in some embodiments of the invention. A difference from a full colon preparation regime, in some embodiments of the invention, is that the laxative dose administered is chosen, not for the purpose of fully cleansing the colon, but rather for the purpose of bringing the colon contents to the point where a colon cleansing device is capable of handling the amount and/or the consistency of waste residing in the colon.

Exemplary Colon Wall Clearance Scenarios

Descriptions are now presented of exemplary operations, preparations, and/or conditions for clearance of a colon wall for diagnostic observation, for example, during a colonoscopy.

Exemplary No-Preparation Wall Clearance

In some embodiments of the invention, a patient arrives to the colonoscopy table without previous preparation of the colon in anticipation of the exam. This occurs, for example, due to an urgent need for colonoscopic examination (for example, if bleeding is noted), or simply because of confidence (perhaps due to information obtained in a previous interview) that a patient's normal bowel state is adequate for obtaining good colonoscopy results in tandem with a colon cleansing device.

In some embodiments of the invention, the patient has eaten, for example, within the last 2-4 hours, 3-6 hours, 4-8 hours, 6-12 hours, 10-20 hours, or another recent range of periods having the same, intermediate, larger and/or smaller bounds. Such ranges of periods are applicable as well to reduced preparation procedures, wherein some modification of diet, administration of laxative, and/or other preparatory procedure or instruction has occurred or been given.

With the understanding that any of the particle types described hereinabove are potentially present in an unprepared colon, in some embodiments of the invention, colon wall cleansing comprises any combination of the non-preparation strategies described hereinabove, in any order necessary to obtain a good diagnostic view of the colon. Any of the colon wall cleansing strategies described hereinabove are optionally usable during any portion of a colonoscopy. Nevertheless, the phases of insertion and withdrawal of the probe are potentially distinct in which cleansing strategies are most effectively employed.

In some embodiments of the invention, strategies of reduction and evacuation are primarily used during insertion of a colonoscope probe toward the distal end of a colon. Potentially, fecal masses encountered impede distal progress until they are dealt with, for example, by disaggregation. Additionally or alternatively, it is a potential advantage to use the time required for distal insertion of the colonoscope probe as active waste evacuation time as well, since, for example, there is potentially a limit to the rate at which matter can be evacuated through a waste evacuation channel. It is optional, however, to fully cleanse intestinal wall during insertion, particularly for embodiments of the invention with which the main phase of diagnostic viewing and evaluation is during colonoscope probe withdrawal.

In some embodiments of the invention, strategies of shunting and/or identification are most used during withdrawal of a colonoscope from a colon, which is typically when colon wall viewing is most focused on diagnostic evaluation. Insofar as this is a phase of the colonoscopy more focused on diagnostic evaluation, it is correspondingly more important to obtain clear views of portions of the colon wall as they pass by. Furthermore, particles which are shunted distally into the colon are unlikely to present further obstacles to viewing if the colonoscope is being withdrawn, so it is a potential advantage to use the shunting strategy most actively during this phase of the procedure.

Partial Fecal Matter Disaggregation and Monitoring

In some embodiments of the invention, colon wall clearance comprises disaggregation of fecal masses, with shunting of the disaggregated fragments to new positions as necessary. Optionally, fecal matter evacuation as such serves an adjunct function to this fecal mass disruption. In some embodiments, mechanical disruption, for example by fluid irrigation (optionally, comprising fluid jets) breaks apart a fecal mass into smaller fragments which come away from a region of colon wall targeted for observation. Subsequent and/or concurrent evacuation of irrigation fluid balances volume and/or pressure inside the colon. Smaller waste particles suspended in the fluid are optionally evacuated therewith. Larger particles are optionally left alone, "kicked" to another portion of the colon, and/or broken down further, depending, for example, on their position and/or the degree to which they are liable to interfere with further viewing operations.

In some embodiments of the invention, operations targeted to colon wall clearance are monitored through effects on parameters other than wall clearance as such. In some embodiments of the invention, colon cleaning is performed to a criterion of completion based on current evacuation fluid contents.

Indirect bowel clearance criteria can help to overcome viewing limitations during colon cleaning. For example, a relatively restricted view of the bowel contents is available at any given time during a colonoscopy procedure. Bowel contains accessible for removal, however, may be outside this restricted view. This is potentially of particular note during irrigation itself, when fluid is circulating such that it actively obscures the field of view of the colonoscope probe. Potentially, using one or more indirect criteria to determine a need for continued cleaning mitigates these problems.

Even when a targeted portion of colon wall is unambiguously cleared relatively rapidly by fecal mass fragmentation, there is a potential advantage in continuing irrigation and/or evacuation until more of the residual fecal mass is removed from the colon. Fluid-suspended particles in particular are subject to freedom of movement during the procedure as the patient is moved—and fluid drains to different portions of the colon—whereby fecal matter is potentially preferably controlled by removal rather than by shunting away.

Nevertheless, excessive time spent evacuating fecal content is potentially at the expense of lowered diagnostic viewing time, longer procedure time, and/or lowered procedure success. Also, the time and/or effort required to disaggregate fecal matter to the point where particles are small enough to be evacuated from a colon is potentially subject to diminishing returns. For example, initial disaggregation may proceed rapidly as large particles break away from each other and/or as small particles are loosened from a fecal mass to which they adhere. But the initially disaggregated fragments potentially comprise fecal particles which are more resistant to sub-fragmentation, and/or simply too numerous to efficiently target. The degree to which this affects a procedure is itself liable to be variable, depending on the initial state of the bowel and its contents.

In some embodiments of the invention, a determination to continue irrigation and/or evacuation is based on monitoring of the waste content of currently and/or recently evacuated irrigation fluid. Optionally, color, turbidity, optical density, particle count, particle relative volume, qualitative visual appearance (for example "clear", "clear with clots", "brown", "yellow", and/or "cloudy"), and/or another property of the evacuated irrigation fluid is used to monitor particle content.

In some embodiments, a clearing and/or relative clearing of fecal content from evacuated fluid comprises an indication that fecal clearance is reaching a point of diminishing value in the current position of the cleaning system.

Optionally, irrigation and/or evacuation are halted or decreased upon determining that evacuated fluid is or is becoming clear, changing color, or on the basis of another indication of reduced fecal content. Fecal content reduction which leads to irrigation and/or evacuation rate changes comprises, for example, a reduction of 50%, 80%, 90%, 95%, and/or 100% relative to a baseline fecal content. Baseline fecal content is, for example, a peak fecal content, and/or a recent average fecal content, as measured by one or more monitored parameters.

Optionally, irrigation by liquid (such as water, isotonic saline, or another fluid) is reduced while evacuation continues to drain remaining liquid. Reduction is, for example, by 80%, 60%, 40%, 20%, or another larger, smaller, or intermediate fraction. Optionally, evacuated liquid volume is balanced by a supply of gas (air, $CO_2$, or another gas) to maintain overall insufflation volume.

Additionally or alternatively, in some embodiments of the invention, repositioning of the colon cleansing apparatus is performed based on observation of a reduced particle content in evacuated fluid. Optionally, evacuation continues during repositioning, and/or restarts after repositioning.

In some embodiments of the invention, evaluation of evacuated fluid particle content comprises automatic measurement based on optical sensing, for example, digital particle counting or light transmission properties. In some embodiments, another automatic measurement of evacuated irrigation fluid properties is used, for example, electrical conductivity, viscosity, and/or pressure. In some embodiments, the point of measurement is, for example, within an evacuation lumen, or at an entrance thereto or exit therefrom. Additionally or alternatively, monitoring is performed on the contents of a temporary accumulation chamber (an "integrating chamber") comprising a widening located along the evacuation lumen and/or within a receiving tank for evacuated fluid.

In some embodiments, monitoring is performed at one or more points external to the evacuation lumen within the colon. In some embodiments of the invention, a non-imaging means of evaluating regional fecal content is used. For example, an optical sensor and/or an illumination/optical sensing pair is provided at one or more points near the distal end of the evacuation lumen, and/or along the length of the evacuation lumen; each pair providing an integrated view of local spectral properties of the colon wall. Potentially, the spectral distribution of light returned to the sensor provides an indication of fecal matter distribution in the colon. Additionally or alternatively, sensors for conductance, osmotic pressure, or another physical or chemical parameter are provided for the determination of fluid content distribution.

In some embodiments of the invention, irrigation and/or evacuation activation and/or stoppage comprises at least partially automated operation according to automatically sensed conditions of waste presence. For example, a bi- multi- or continuously variable speed of irrigation and/or evacuation is superimposed on user-provided commands, based on determination of the presence of waste particles suitable for evacuation in the region of the evacuation intake aperture.

Adjustable Intake Aperture Size

In some embodiments, the effective minimum size of coarse particles—as defined, for example, hereinabove in relation to an evacuation lumen; and as determined, for example, by inlet dimensions to an evacuation lumen—determines which particles are excluded from evacuation. In some embodiments, this determination is such that a fraction of fecal matter is generally left behind after all medium and smaller particles are removed. The portion of coarse particles out of all fecal matter originally present is, for example, 5%-10%, 8-15%, 10-20%, or another range having bounds which are the same, intermediate, larger and/or smaller. In some embodiments, the cross-section of the evacuation lumen itself determines the minimum size of coarse particles. In some embodiments, evacuation through an evacuation lumen comprises passage through a screening aperture which is sized to be smaller than the cross-section of the evacuation lumen. In some embodiments, the screening aperture is the aperture of the evacuation lumen itself. In some embodiments, one or more screening apertures are comprised in and/or defined by a screening structure which guards access into the evacuation lumen. In some embodiments, the screening structure is a mesh and/or grid-work of apertures. In some embodiments, screening structure comprises a partial barrier such as a post, septum, flap, or other structure which partially or fully crosses in front of an intake aperture. In some embodiments of the invention, size exclusion at the intake side of an evacuation lumen is such as to reduce the size at which the bounds between coarse particles and medium particles (as defined hereinabove) occurs. Potentially, this reduces a likelihood and/or frequency with which an evacuation lumen is plugged within and along its extent, due, for example, to a reduction in the maximum size of medium particles.

In some embodiments of the invention, the screening aperture size is adjustable. Potentially, this allows a preferred compromise between in-lumen blockage and lumen-intake blockage rates to be set. The range of adjustments is, for example, 10-100%, 50-100%, 80-100%, or another range having the same, intermediate, and/or lower bounds of a maximum size. Maximum size is, for example, a diameter of 3-5 mm, 3-5 mm, 4-7 mm, or another range having the same, intermediate, lower and/or greater bounds.

In some embodiments, the screening aperture is set before a procedure begins, based on an understanding of the state of the colon contents—for example, the relative mix of small, medium, and coarse particles and/or their compositions expected. Optionally, a relatively larger aperture is chosen when the particles are expected to be generally either too large to enter the evacuation aperture at all, or too small and/or delicate to create blockages during evacuation. Optionally, a relatively smaller aperture is chosen when the particles near the medium/coarse boundary are expected to be numerous and/or prone to formation of internal lumen blockages. In some embodiments, screening aperture adjustment is by positioning of an element such as a shutter, septum, or post; inflation of an element such as a balloon; modification of a screening structure by cutting, bending, or other modification; and/or selection of a screening structure based, for example, on aperture size.

In some embodiments, a screening aperture is adjustable during a procedure, for example by remotely adjusting the position and/or size of an occluding member. In some embodiments, an occluding member comprises a shutter. Optionally, the shutter is coupled to a motive force such as a piezoelectric device. Optionally, the shutter is coupled to a motive force by a cable or pressure line. In some embodiments, an occluding member comprises an inflatable element. Optionally, the inflatable element size is adjusted by a pressure conveyed, for example, from a pressure source used for evacuation and/or irrigation, or by an independent pressure source. Optionally, a valve member is actuatable to switch between a "pressure set" mode, wherein it is coupled to the pressure source, and a "fixed pressure mode", wherein it is sealed off from the pressure source.

Exemplary Low-Preparation (Dietary and During Procedure) Wall Clearance

In some embodiments of the invention, a patient who is scheduled to undergo a colonoscopy is provided with and follows instructions for dietary modification before the procedure itself. Potentially, following these instructions modifies and/or helps to assure the quantity and/or nature of colon contents for more effective colon wall cleansing and/or greater assurance of a successful colonoscopy procedure.

In some embodiments, dietary modification begins, for example, 4 hours, 8 hours, 12 hours, 24 hours, 36 hours, 48 hours, 60 hours, or another longer, shorter, or intermediate period before a scheduled colonoscopy procedure. A shorter time potentially reduces disruption of a patient's normal routine. A longer time potentially increases the effectiveness of the dietary modification, at least up to the limit of the transit time of food through the patient's digestive tract.

In some embodiments, dietary modification comprises ensuring that all fruit and vegetable matter which is consumed during the period of dietary modification lacks coarse seed and/or shell or peel fragments, and/or is structurally degraded to remove coarse spongy and/or fibrous particles from the stool. This is achieved, for example, by one or more of the following: avoiding seed matter, removing peels, thoroughly cooking food (for example, by boiling), and/or reducing portions to small ingested particle sizes (for example, by blending). In some embodiments, such dietary precautions are required for other foods consumed, such as meats. Optionally, food types which are well-broken down by ordinary passage through the gut (including but not limited to, for example, eggs, breads, and dairy products) are allowed to be consumed without special modification. Optionally, amounts and/or relative amounts of foodstuffs consumed are regulated to stay within a guideline, for example, to reduce overall amounts of fecal matter (by reducing food intake), and/or to help establish a certain fecal consistency (for example, by requiring a minimum level of dietary fiber).

In some embodiments of the invention, during a period of dietary modification, a minimum portion of fruits and/or vegetables (or another source of dietary fiber) is advised and/or consumed, in order to reduce the prevalence of hard stool particles in the colon during the colonoscopy procedure.

In some embodiments, a time-varying diet is recommended and/or followed. For example, the early diet, in some embodiments, is weighted particularly toward a high level of dietary fiber, in order to ensure that older fecal particles (which are potentially the driest and/or hardest) present at the time of examination remain relatively soft. The later diet, in some embodiments, is more weighted toward consumption of low-residue foods, optionally with a corresponding reduction in foods high in dietary fiber. Potentially, this decreases fecal volume in the distal reaches of the colon, but without a corresponding increase in fecal hardness, due to a decreased passage of time for water re-absorption for such fecal material.

In some embodiments of the invention, a patient's present colon state is taken into account in providing dietary instructions. For example, a patient who has been experiencing constipation, bowel movements with low Bristol stool scores (1 or 2), and/or a low rate of bowel evacuation (for example, less than once a day) receives, in some embodiments, a diet having an increased level of dietary fiber (more fruits and/or vegetables). Alternatively, a patient with already loose, soft, and/or frequent bowel movements is optionally given dietary instructions which ensure reduced particle size, without alteration to food type.

Exemplary Low-Preparation (Dietary, Moderate Laxative) Wall Clearance

In some embodiments of the invention, moderate laxative administration is used to reduce fecal volume, prevent coarse particle buildup (such as concretion particles), and/or to purge the colon of coarse particles which are potentially initially present in the colon.

In some embodiments, a moderate laxative has an effect like, and potentially itself comprises, dietary fiber. Potential uses and advantages of deliberately increased amounts of dietary fiber are discussed hereinabove.

In some embodiments, a moderate laxative is administered to prevent fecal volume buildup, speeding the passage of food through the colon without the administration reaching a level which cleanses the colon. In some embodiments, moderate laxative administration ensures that stool becomes and/or remains soft in the period leading up to a scheduled examination.

In some embodiments of the invention, laxative administration is variable over the time leading up to the colonoscopy examination. For example, a course of laxatives is optionally begun at about the time that a low-preparation diet (for example, one as described hereinabove) is begun, but ending shortly thereafter. A potential advantage of this is to purge the colon of potentially coarse pre-existing material. Optionally, the course of laxatives is not continued until the examination, however, since it is understood that new food intake will conform to the requirements for good colon wall cleansing. Optionally, the laxative is administered only if there is a determination of a pre-existing condition of hard stool, infrequent bowel movements, or the like. In some embodiments of the invention, the laxative course lasts for 4 hours, 8 hours, 12 hours, or another larger, smaller, or intermediate length of time. In some embodiments, the course of laxative administration begins 60 hours, 48 hours, 36 hours, 24 hours, 12 hours, or another period longer, shorter or intermediate in length before the examination.

As used herein the term "about" refers to within ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

What is claimed is:

1. A channel for evacuating fecal waste from a human colon, comprising:
    a lumen, sized for insertion of a distal end thereof to a distal end of said colon;
    said lumen having a lobed cross-section comprising at least a first and second lobe;
    a passage between said first and second lobes comprising at least one slot narrower than the widest extent of the cross-section of said first lobe;
    said first lobe having a cross-sectional area at least 4 times larger than the cross-sectional area of said second lobe; and
    wherein fluid between said first and second lobe is gated by a one-way valve member extending along said slot.

2. The waste evacuation channel of claim 1, wherein said channel is enclosed by a wall constructed to resist collapse under application of a pressure differential of at least 0.2 Atm lower within the lumen than surrounding pressure.

3. The waste evacuation channel of claim 1, wherein the valve member comprises a flap which extends to a proximal end of said slot, but terminates at least 1 cm before a distal end of said slot.

4. The waste evacuation channel of claim 1, wherein the valve member resists passage of fluid into said second lobe under pressure from said first lobe, more than it resists passage of fluid from said second lobe to said first lobe under equivalent reversed pressure.

5. The waste evacuation channel according to claim 1, wherein:
    external access into said lumen at said distal end of said lumen is through at least one intake aperture and said at least one aperture is configurable from among a plurality of different sizes.

6. The channel of claim 5, wherein the size of said aperture is configurable by adjustment while said lumen is inserted into said colon.

7. The channel of claim 6, wherein said size of said aperture is configurable by adjustment of pressure at said distal end of said channel.

8. The waste evacuation channel according to claim 1, wherein said second lobe comprises at least one groove.

* * * * *